United States Patent [19]

Gokel et al.

[11] Patent Number: 4,631,119
[45] Date of Patent: Dec. 23, 1986

[54] REVERSIBLE, ELECTROCHEMICALLY-SWITCHED LARIAT ETHERS

[75] Inventors: George W. Gokel; Luis Echegoyen, both of Miami, Fla.

[73] Assignee: W. R. Grace & Co., New York, N.Y.

[21] Appl. No.: 736,993

[22] Filed: May 22, 1985

Related U.S. Application Data

[63] Continuation-in-part of Ser. No. 554,686, Nov. 23, 1983, abandoned.

[51] Int. Cl.$^4$ .............................................. C25C 1/00
[52] U.S. Cl. ................................................. 204/59 R
[58] Field of Search .................. 204/59 R, 72 R, 73 R

[56] References Cited

U.S. PATENT DOCUMENTS 3,952,015 4/1976 Krespan .............................. 260/338
4,436,923 3/1984 Pacey et al. .......................... 549/352
4,482,435 11/1984 Torii et al. ......................... 204/59 R

FOREIGN PATENT DOCUMENTS 8204253 12/1982 World Int. Prop. O.

OTHER PUBLICATIONS

Gokel, G. W., Dishong, D. M., Diamond, C. J., J. Chem. Soc. Commun., 1980, 1053.
Dishong, D. M., Diamond, C. J., Gokel, G. W., Tetrahedron Letters, 1981, 1663.
Schultz, R. A., Dishong, D. M., Gokel, G. W., Tetrahedron Letters, 1981, 2623.
Dishong, D. M., Diamond, C. J., Cinoman, M. I., Gokel, G. W., J. Am. Chem. Soc., 1983, 105, 586.
Shinkai, S., Shigematsu, K., Kusano, Y., Manabe, O., J. Chem. Soc. Perkin Trans. I, 1981, 3279.
Shinkai, S., Minami, T., Kusano, Y., Manabe, O., Tetrahedron Letters, 1982, 2581.
Nakamura, H., Nishida, H., Takagi, M., Ueno, K., Bunseki Kagaku, 1982, 31, E131.
Shinkai, S., Ogawa, T., Kusano, Y., Manabe, O., Kibukawa, K., Goto, T., Masuda, T., J. Am. Chem. Soc., 1982, 104, 1960.
Shinkai, S., Minami, T., Kusano, Y., Manabe, O., J. Am. Chem. Soc., 1982, 104, 1967.
Shinkai, S., Minami, T., Kouno, T., Kusano, Y., Manabe, O., Chemistry Lett., 1982, 499.
Takahashi, M., Takamoto, S., Bull Chem. Soc. Jpn., 1977, 50, 3413.
Stetter, H., Frank, W., Angew. Chem. Int. Ed. Engl., 1976, 15, 686.
Desreux, J. F., Inorg. Chem., 1980, 19, 1319.
Stetter, H., Frank, W., Mertens, R., Tetrahedron, 1981, 37, 767.
Tazaki, M., Nita, K., Takagi, M., Ueno, K., Chemistry Lett., 1982, 571.
Nakamura, H., Nishida, H., Takagi, M., Ueno, K., Analytica Chim. Acta, 1982, 139, 219.
Charewicz, W. A., Bartsch, R. A., Analytical Chem., 1982, 54, 2300.
Shinkai, S., Kinda, H., Araragi, Y., Manabe, O., Bull. Chem. Soc. Jpn., 1983, 56, 559.
Tsukube, H., J. Chem. Soc. Perkin Trans. I, 1983, 29.
Tsukube, H., J. Chem. Soc. Perkin Trans. I, 1983, 29.
Gatto, V. J., Gokel, G. W., J. Am. Chem. Soc. 1984, 106, 8240.
Hammett, L. P., Physical Organic Chemistry, Second Edition, McGraw Hill Book Co., 1970, pp. 355-357.
Stryer, L., Biochemistry, W. H., Freeman & Co., Second Edition, 1981, p. 28.
Minami, T., Shinkai, S., Manabe, O., Tetrahedron Lett., 1982, 5167.

Primary Examiner—R. L. Andrews
Attorney, Agent, or Firm—Richard P. Plunkett; William W. McDowell, Jr.

[57] ABSTRACT

This invention relates to novel heteromacrocyclic compounds which have electrochemically reducible sidearms containing uncharged Lewis basic donor groups appropriately placed to interact with a macroring-bound cation and an electrochemical switching process utilizing same. Reduction of the sidearm's aromatic residue produces a radical anion species. The resulting ligand binds a cation more strongly than does the neutral species. These compounds are therefore of utility as electrochemically controlled cation binders.

1 Claim, 4 Drawing Figures

FIG. 1 DATA FOR COMPOUND I
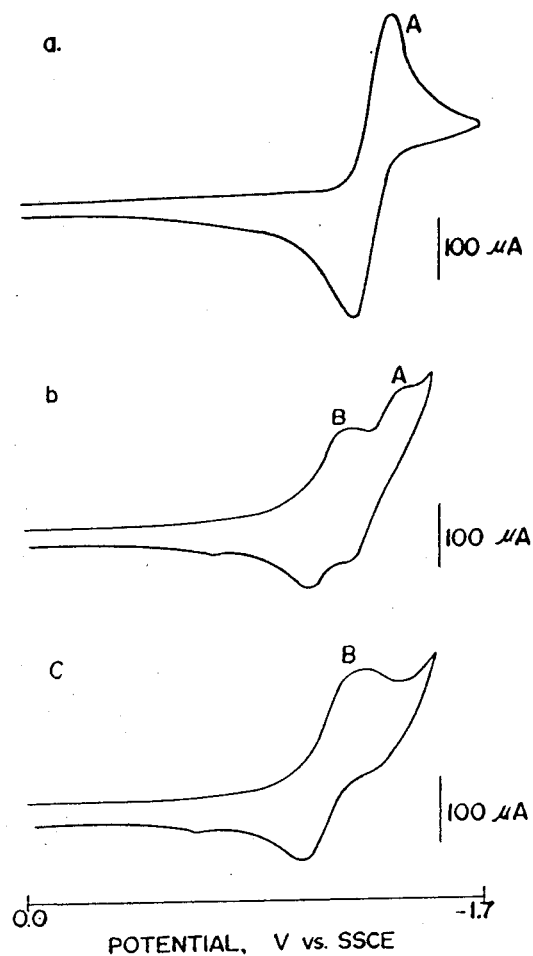

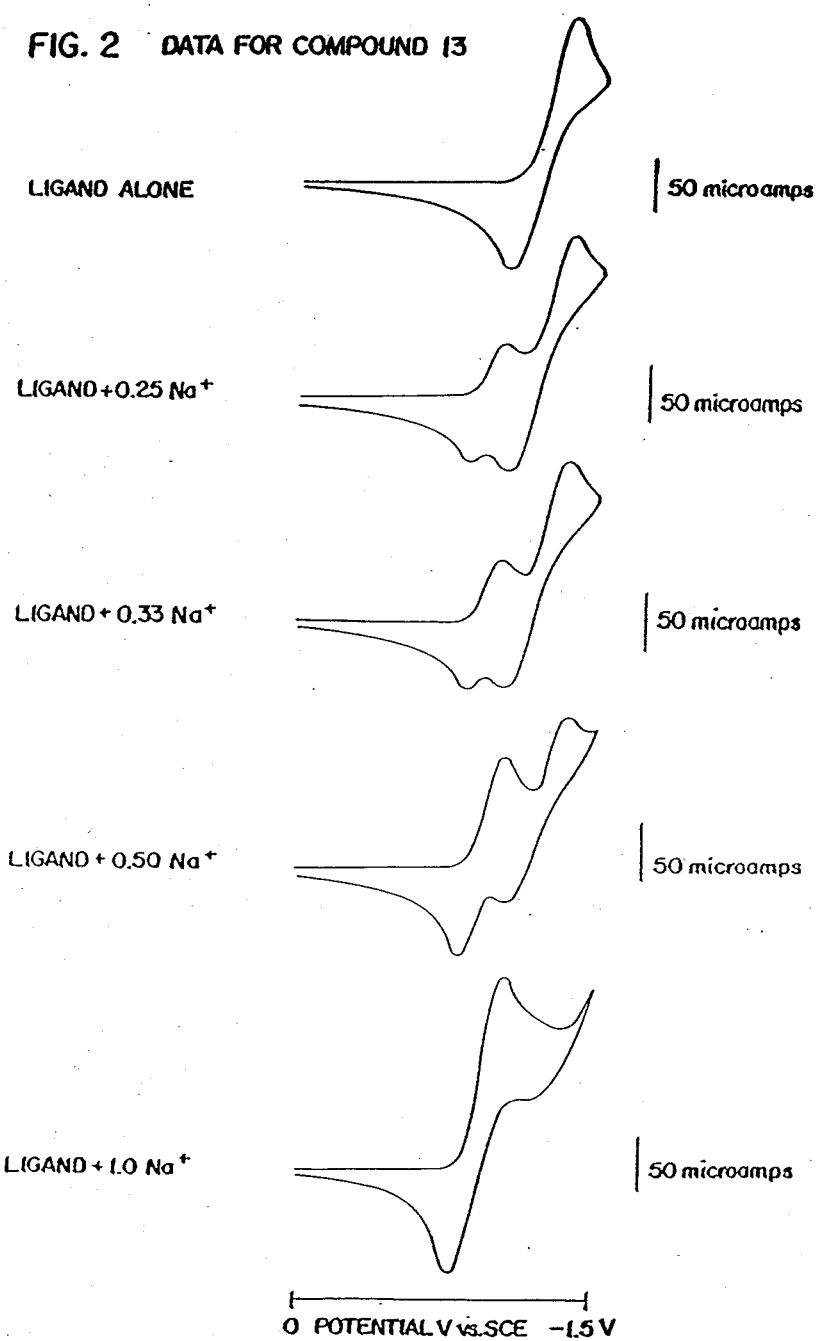

FIG. 3  DATA FOR COMPOUND 24
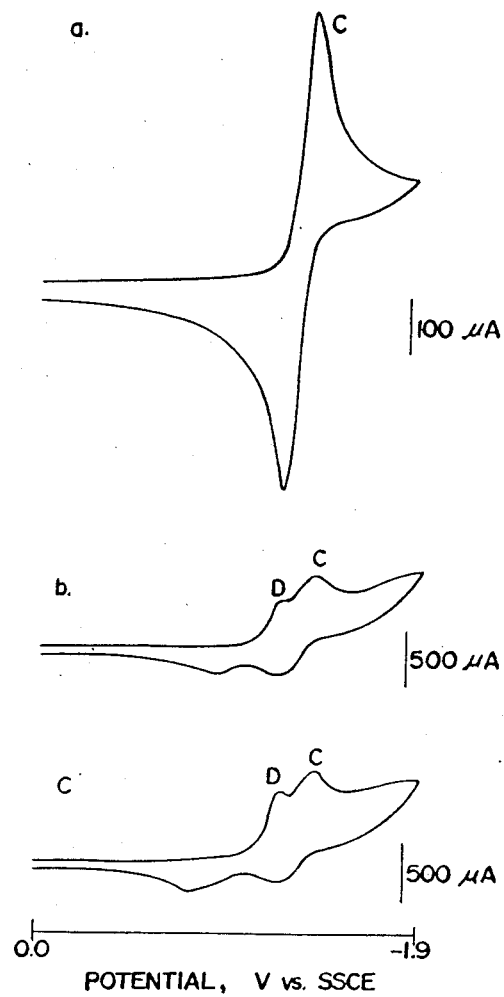

FIG. 4  DATA FOR COMPOUND 26
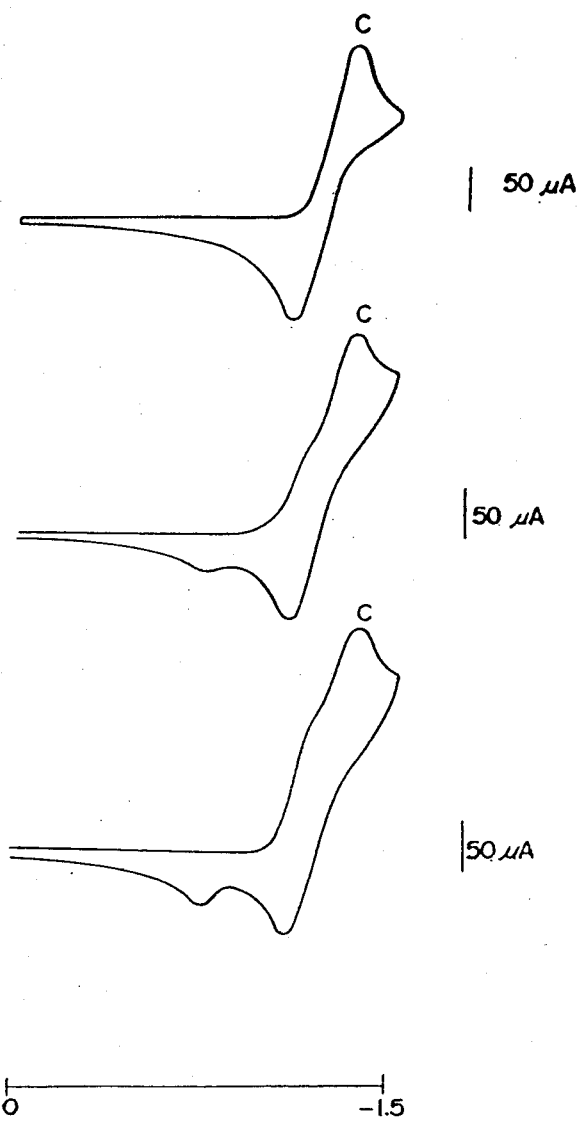

REVERSIBLE, ELECTROCHEMICALLY-SWITCHED LARIAT ETHERS

This application is a continuation in part of application Ser. No. 554,686, filed Nov. 23, 1983, and now abandoned.

BACKGROUND OF THE INVENTION

1. Field of the Invention

This invention is directed to novel heteromacrocyclic compounds (herein sometimes referred to as lariat ethers) which, due to the incorporation of three features, i. e., macroring, sidearm and electron-deficient aromatic species, affords a cation with a three-dimensional array of binding sites. The invention is also directed to an electrochemical switching process utilizing said lariat ethers wherein they can be reversibly converted from a weaker to a stronger cation binder. Although electron transfer herein is shown only by an electrochemical method, reduction may also be accomplished by reaction with chemical reducing agents such as sodium or potassium metal.

Several features are essential to the present invention. These include a macrocyclic polyether ring capable of binding a cation such as sodium within it. Examples of macrocyclic rings known in the literature which can do so range from 12-60 members. A macrocyclic polyether ring capable of binding cations is a necessary, but not sufficient condition of the instant invention. A sidearm or tether of some sort is necessary to attach the aromatic residue to the macroring. This is also a necessary, but not sufficient condition. Finally, the aromatic residue must be sufficiently electron deficient that it can accept an electron and form a radical anion. Implicit in this is the notion that the electron attracting group or groups, which make the aromatic residue susceptible to reduction, must also be capable of interacting as donor groups with the ring-bound cation, thusly:

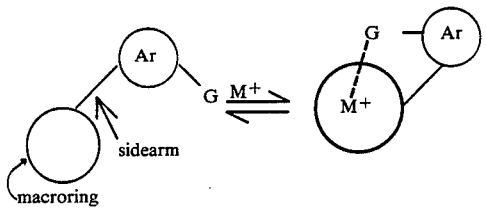

Any person skilled in the art can use this three-part concept and utilize the invention by conducting the following steps. First, a macroring would be chosen. According to our specification, the ring would contain from 12-36 atoms selected from the group C, N, O or S. Second, a decision would be made concerning the point of attachment to be used for the sidearm. Since the ring consists only of C, N, O and S, and since the latter two elements are normally divalent, and since both valences of a divalent species must be utilized to form a ring, either carbon or nitrogen would be chosen as the point of attachment (hereinafter referred to as the pivot atom) for each sidearm bearing an electron deficient residue. Third, a sidearm would be selected. According to our specification, the sidearm could contain a variety of atoms and arrangements thereof. The key consideration is that, when the aromatic residue is attached to the sidearm, the correct geometrical relationships of the present invention must apply. Obviously, the appropriateness of the relationship can only be determined after an electron deficient aromatic residue is selected. If the aromatic residue selected is, for example, 2-nitrophenyl, the sidearm can be shorter than if the residue selected is 3-nitrophenyl to utilize the instant invention. One could prepare a molecular model, have a computer graphics program plot a structure or use any other technique which would allow the appropriate length and geometric relationship of the sidearm to be determined. Any such determination would take account of known geometrical relationships and inherent molecular flexibilities in accord with the rules of conformational analysis well known to those skilled in this art.

2. Description of the Prior Art

"Lariat Ethers" having appropriately placed sidearms can, in many cases, enhance the binding between a ligand and cation as compared to the binding level observed for a simple, monocyclic system. See 1, (a) Gokel, G. W., Dishong, D. M., Diamond, C. J., J., Chem. Soc. Chem. Commun., 1980, 1053; (b) Dishong, D. M., Diamond, C. J., Gokel, G. W., Tetrahedron Letters, 1981, 1663; (c) Schultz, R. A., Dishong, D. M., Gokel, G. W., Tetrahedron Letters, 1981, 2623; and (d) Dishong, D. M., Diamond, C. J., Cinoman, M. I., Gokel, G. W., J. Am. Chem. Soc., 1983, 105, 586.

Binding strength has been altered in crown ethers and cryptand compounds by photoswitching. See 2. (a) Shinkai, S., Shigematsu, K., Kusano, Y., Manabe, O., J. Chem. Soc. Perkin Trans. I, 1981, 3279; (b) Shinkai, S., Minami, T., Kusano, Y., Manabe, O., Tetrahedron Letters, 1982, 2581; (c) Nakamura, H., Nishida, H., Takagi, M., Ueno, K., Bunseki Kagaku, 1982, 31, E131; (d) Shinkai, S., Ogawa, T., Kusano, Y., Manabe, O., Kibukawa, K., Goto, T., Masuda, T., J. Am. Chem. Soc., 1982, 104, 1960; (e) Shinkai, S., Minami, T., Kusano, Y., Manabe, O., J. Am. Chem. Soc., 1982, 104, 1967; and (f) Shinkai, S., Minami, T., Kouno, T., Kusano, Y., Manabe, O., Chemistry Lett., 1982, 499.

Ionization of acidic functions (both in the ring and on pendant groups) has also been used for this purpose. See 3. (a) Takahashi, M., Takamoto, S., Bull Chem. Soc. Jpn., 1977, 50, 3413; (b) Stetter, H., Frank, W., Angew. Chem. Int. Ed. Engl., 1976, 15, 686; (c) Desreux, J. F., Inorg. Chem., 1980, 19, 1319; (d) Stetter, H., Frank, W., Mertens, R., Tetrahedron, 1981, 37, 767; (e) Tazaki, M., Nita, K., Takagi, M., Ueno, K., Chemistry Lett., 1982, 571; (f) Nakamura, H., Nishida, H., Takagi, M., Ueno, K., Analytica Chim. Acta, 1982, 139, 219; (g) Charewicz, W. A., Bartsch, R. A., Analytical Chem., 1982, 54, 2300; and (h) Shinkai, S., Kinda, H., Araragi, Y., Manabe, O., Bull. Chem. Soc. Jpn., 1983, 56, 559.

Analogously, protonation of amines has been used to alter the binding strength. See 4. (a) Tsukube, H., Tetrahedron Letters, 1983, 24, 1519, and (b) Tsukube, H., J. Chem. Soc. Perkin Trans I, 1983, 29.

Compound 7, shown on page 19 of PCT WO No. 82/04253 shows a superficial resemblance to the claimed compounds. It is not related to the compounds claimed herein because, although it clearly bears a reducible pendant residue, no donor group in the sidearm is in a position to interact with a ring-bound cation. Both the azo linkage and the nitro group are in the para positions. The nitro group is especially remote and would remain so even if the azo linkage could somehow be isomerized from the stable trans ground state to the less stable cis form.

The compounds disclosed in U.S. Pat. No. 4,436,923 are macrocyclic polyether compounds containing pendant nitroaromatic residues. Since they are polysubstituted aromatic residues, even after the obvious deprotonation of the secondary amino group takes place during reduction, the nitroaromatic group could still undergo reduction. This is irrelevant, however, since the reducible aromatic residue is attached to a second aromatic residue which is integral to the macrocycle. The nitro groups could not reach farther than the aromatic ring to which they are attached and thus could not interact with a ring-bound cation when reduced. This is especially true in the reduced form when electron spin is distributed over the nitro groups making them flat.

In addition, the compounds fail to meet the specification of the instant application, said macrocyclic ring must have at least one pendant group attached to either carbon or nitrogen contained within the ring structure. The compounds of U.S. Pat. No. 4,436,923 are attached to a nitrogen atom further attached to an aromatic residue, the latter of which is part of the ring structure.

The compounds of general formula (1) shown in Japanese Pat. No. 57-4976 might seem to meet the specifications set forth in the claims of the instant patent. This is not true for two reasons. When an acidic proton and a protonatable amine are present in the same molecule, the inherent cation binding of the species is dramatically reduced. Although no homogeneous equilibrium cation binding data are available in the Japanese patent, information bearing directly on this particular case is available from some recent work of our own which may be found in Gatto, V. J., Gokel, G. W., J. Am. Chem. Soc. 1984, 106, 8240. Therein, potassium cation binding constants for N-(2-methoxybenzyl)-4,13-diaza-18-crown-6 and N-(2-hydroxybenzyl)-4,13-diaza-18-crown-6 are reported. In the hydroxy compound, which is the direct analog (without the nitro group) of the Japanese compound, the potassium cation binding constant (Ks, in methanol) is 389 (log Ks=2.59). The corresponding methoxy compound has a potassium cation binding constant also in anhydrous methanol solution of 87,000 (log Ks=4.94). This tremendous difference is due to intramolecular proton transfer from phenolic hydroxyl to tertiary nitrogen. Such a proton transfer is likely to be much more substantial when a nitro group is present in the phenol since nitro is such a strongly acidifying function. Indeed, the pKa values for phenol and para-nitrophenol are, respectively, 9.89 and 7.15. Note that the lower the pKa value, the greater the acidity. Converting the logarithmic values to equilibrium constants, the nitrophenol is more than 500 times more acidic than the unsubstituted phenol. This means that proton transfer will be 500 times more of a problem for the nitrophenol than for phenol.

The problem with respect to the instant invention is that, when proton transfer occurs as we have shown conclusively that it will with these phenols, a phenoxide anion is produced. The oxygen anion is strongly electron releasing which will substantially increase the redox potential of any attached aromatic ring. If the —OH group was replaced by —OCH$_3$, the compound would be similar to ortho-nitronanisole and still reducible. According to the Hammett (sigma para) constants [Hammett, L. P.; Physical Organic Chemistry, second edition, McGraw Hill Book Co., 1970, pages 355-357], only amino and dimethylamino among common substituents are more electron releasing than —O$^-$. The compounds reported by Ueno are designed to be deprotonated easily to give colored anions which will complex with calcium cation.

In U.S. Pat. No. 3,952,015, "X" contained within the macroring may be ". . . O or NH, N-alkanoyl, N-benzoyl wherein the benzene ring is optionally substituted with —NO$_2$, —NH$_2$ or —CH$_3$ . . .". The N-alkanoyl residues are irrelevant to the instant application since they contain no readily reducible groups. The N-benzoyl group, when substituted by nitro, is reducible at an accessible potential. Note, however, that N-benzoyl must be attached to tne macroring through an —N—CO—Ar linkage. Such linkages are always planar having 20 kcal/mole of resonance energy in each amide bond. Indeed, the amide or peptide link is described by Stryer in his standard biochemistry text [Stryer, L., Biochemistry, W. H. Freeman and Co., Second Edition, 1981, p. 28] as a "rigid and planar" unit. This is, of course, a key feature in the structures of peptides. The compounds alluded to in U.S. Pat. No. 3,952,015 would not be relevant in any event if the nitro group was attached to the benzene ring in either the 3- or 4-position. When it is attached at the 2-position, (i. e., ortho, it is also irrelevant since the ring must be coplanar with the —N—CO— link. Likewise, the nitro group will favor coplanarity with the aromatic ring, and the nitro group will be incapable of interacting with a ring-bound cation. Even if the adjacent —N—CO— and —NO$_2$ groups are distorted, the pendant aromatic ring cannot reach back over the macroring. Finally, crown compounds have been structurally altered by oxidative dimerization of attached sulfhydryl groups. See Minami, T., Shinkai, S., Manabe, O., Tetrahedron Lett., 1982, 5167. Like the other prior art discussed above, none incorporated all three features, i. e., macroring, sidearm and electron-deficient aromatic residue of the lariat ethers in the correct geometrical relationships of the present invention to produce a switching mechanism.

One object of the instant invention is to produce novel heteromacrocyclic compounds capable of offering a cation a three-dimensional array of donor groups. Another object is to produce heteromacrocyclic compounds which increase cation binding power when reduced. Still another object of the invention is to provide an electrochemical switching process utilizing said heteromacrocyclic compounds wherein they can be reversibly converted from a weaker to a stronger cation binder. Other objects will become apparent from a reading hereinafter.

DESCRIPTION OF THE INVENTION

This invention relates to heteromacrocyclic ring compounds having a sidearm attached to the ring which, in turn, is attached to an electron deficient aromatic residue. These heteromacrocycles are designed to bind various metallic cations by enveloping them in a three-dimensional array of Lewis basic donor groups. These compounds are also designed to undergo reduction to afford radical anion species which have cation binding powers greatly enhanced over those of the neutral species. The reduction-reoxidation of these compounds provides a switching mechanism for increasing cation binding strength. The essential features of the compounds which are the subject of the instant invention are a heteromacrocyclic ring, a sidearm and an electron deficient aromatic residue. Each of these features is explained below.

(1) The heteromacrocyclic ring is composed of from 12-36 atoms, i.e., within the range of crown ether ring sizes known in the literature. The atoms in the ring are selected from the elements C, N, O and S. When O, N or S is part of the macroring, any two of these elements must be separated by at least two carbon atoms. Included within this invention is the case where positional isomers of the heteroaromatic ring are present, such as 4,7-diaza-12-crown-4 and 4,10-diaza-12-crown-4. Since O and S are divalent in the neutral state, they are otherwise unsubstituted when part of the ring structure. Nitrogen and carbon are tri- and tetravalent in their neutral states and may have, respectively, one or two additional substituents on each element. Allowed substituents on the macroring are hydrogen or alkyl groups having from 1-12 carbons. Carbon within the ring structure may have one or two alkyl groups on each atom but, if two alkyl groups are present, they must both be primary at the point of attachment. Carbocyclic aromatic residues may also substitute the macroring as may carbocyclic aromatic residues attached to alkyl groups wherein the total number of carbon atoms in any substituent does not exceed 12. The pivot atom is an integral part of the heteromacrocyclic ring and is the point at which the sidearm (see below) is attached to the heteromacrocyclic ring. The pivot atom may be carbon or nitrogen.

(2) The sidearm is the molecular tether which connects the electron deficient aromatic residue to the heteromacrocyclic ring. The sidearm is a mechanical connecting unit which plays no role in the switching mechanism except insofar as it brings both macroring and electron deficient aromatic residue into proximity in the correct geometrical relationship. It may contain the elements C, N, O and S. Carbon and nitrogen within the sidearm structure may be substituted by alkyl groups having from 1-12 carbon atoms and the substituent may contain a carbocyclic aromatic residue so long as the total number of atoms in each substituent does not exceed 12 atoms. Further, when two alkyl substituents are present on a single carbon, the alkyl groups must be primary at the point of attachment. The sidearm unit may also be part of a carbocyclic aromatic residue such as 1,2-benzo-, 1,2-naphtho-, 2,3-naphtho- or carbocyclic aromatic derivatives thereof. The sidearm unit may also be part of a heteroaromatic residue such as 2,3-furanyl-, 3,4-furanyl-, 2,3-thiophenyl-, 3,4-thiophenyl-, 2,3-pyridyl-, 3,4-pyridyl- or other five- or six-membered ring aromatic residue. In such cases, the precise identity of the aromatic residue is unimportant so long as it is not more readily reduced than the aromatic residue attached to the sidearm which is the object of the instant invention.

(3) The electron deficient aromatic residue is a carbocyclic aromatic or heteroaromatic residue selected from the group substituted benzene, naphthalene, anthracene, phenanthrene, fluoranthene, benzanthracene, chrysene, triphenylene, naphthacene, perylene, picene, pentacene, pentaphene, furan, thiophene, pyridine, pyridazine, pyrimidine, pyrazine, quinoline, isoquinoline, phthalazine, 1,8-naphthyridine, quinoxaline, quinazoline, cinnoline, carbazole, phenanthridine, acridine, phenanthroline or phenazine. Other electron deficient aromatic residues include, but are not restricted to, picryl, picramyl, phthalimidoyl, biphenyl and fused aromatic derivatives thereof. The aforenamed aromatic or heteroaromatic residues must meet two qualifications to be the subject of the instant invention. First, they must be reducible at a potential below 2.0 V vs. saturated calomel electrode (SCE). Second, they must be substituted by a group containing lone pair electrons which can serve as a donor to a ring-bound cation. Examples of such groups are alkyl or aryl ethers (like —$OCH_3$ or —$OC_6H_5$) or thioethers (like —$SCH_2CH_3$ or —$SCH_2C_6H_5$; F, Cl or Br; amino (—$NH_2$); dialkylamino (—NRR'); nitroso (—N=O); nitro (—$NO_2$); cyano (—CN); trihalomethyl (—$CX_3$ where X may be F, Cl or Br in any combination); carbonyl oxygen as part of an aldehyde, ketone, quinone, ester, amide, urea or carbamate; thiocarbonyl sulfur as part of a thioaldehyde, thioketone, thioester, thioamide, thiourea or thiocarbamate; or other stable, Lewis basic donor group. Typical electron withdrawing substituents found on the electron deficient aromatic residue are F, Cl or Br; nitroso (—N=O); nitro (—$NO_2$); cyano (—CN); trihalomethyl (—$CX_3$ where X may be F, Cl or Br in any combination); ester (—CO—OR, R=alkyl, aryl or substituted derivatives thereof, but not H), amide (—CO—NRR where R=alkyl, aryl or substituted derivatives thereof, but not H), thioester (—CS—OR where R=alkyl, aryl or substituted derivatives thereof, but not H), thioamide (—CS—NRR, where R=alkyl, aryl or substituted derivatives thereof, but not H). The substituents may be present in any position and in any combination so that the net reduction potential of the aromatic residue is below 2.0 V vs. SCE. The aromatic residue may, itself, be electron deficient, as in the case of benzoquinone, naphthoquinone or pyridine. In such cases, the donor group may be a heteroatom contained within the heterocyclic reducible aromatic residue.

Principles for Combining Macroring, Sidearm and Electron-Deficient Aromatic Residue It is well known from the literature, especially recent X-ray crystallographic studies, that the precise geometry of macroring binding is determined by several factors including the identity and oxidation state of the cation bound, the counter-anion, the size of the macroring, the identity and position of the donor groups present in the macroring, the presence of any sidearm, the identity and position of any donor group(s) in any sidearm(s) which may be present in the molecule, and, in the crystals, at least, the presence of water and intermolecular forces. Additional factors may well be involved which are not yet fully understood.

The instant invention depends upon the presence of a macroring which can bind a cation. Attached to the macroring by a molecular tether or sidearm is an electron deficient aromatic residue. When the cation is held within the macroring and proximate to the electron deficient aromatic residue, a remote substituent effect is exerted upon the electron deficient aromatic residue which lowers its reduction potential. When an electron is transferred to the electron deficient aromatic residue and some of that electron density is, in turn, transferred to a donor group proximate to the ring bound cation, it makes the molecule's overall binding strength greater than when the compound is neutral. Structurally, all three elements of the instant invention, i. e., macroring, electron deficient aromatic residue bearing a donor group, and sidearm to connect the two, must be present in an arrangement such that a cation can be bound by and interact with donor groups in both the macroring and on the sidearm's electron deficient aromatic residue. The conformation must be a stable one and metal ion to donor group distances must be near the known bond lengths for such interactions, typically, Li—O, 2.2–2.5 Angstroms, Na—O, 2.3–2.9 Angstroms, Na—N, 2.3–3.0 Angstroms, K—O, 2.7–3.3 Angstroms, K—N, 2.8–3.4 Angstroms, Rb—O, 2.8–3.3 Angstroms, Rb—N, 2.8–3.4 Angstroms, Cs—O, 2.8–3.3 Angstroms, Cs—N, 2.9–3.5 Angstroms. Unless a compound can complex a cation within the cavity created by macroring and side-arm donor groups, and unless the bonding distances for a stable conformation of said molecule are as noted above, the compound is specifically excluded from the instant invention.

Thus, novel compounds operable herein as switching devices include, but are not limited to:

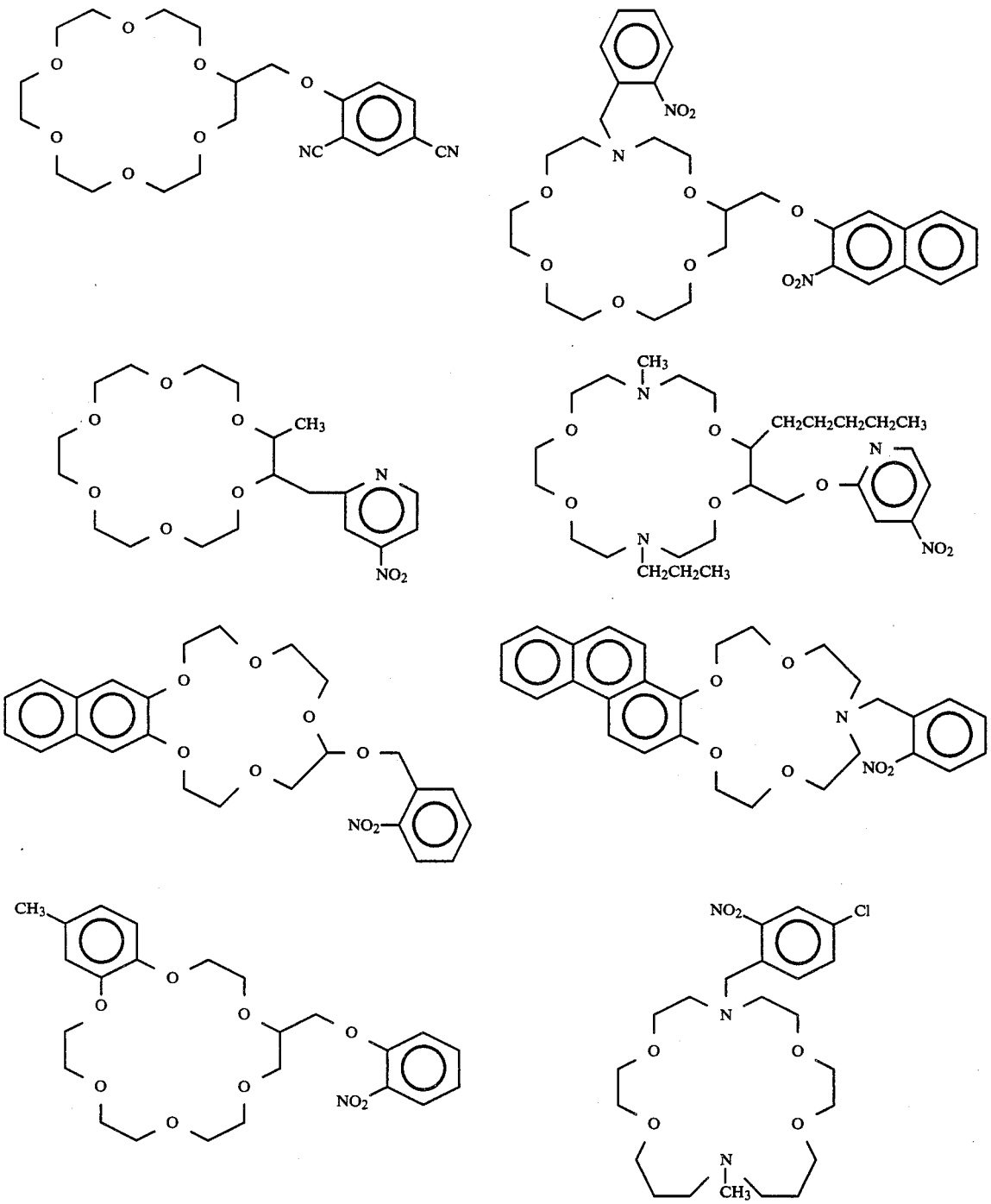

-continued
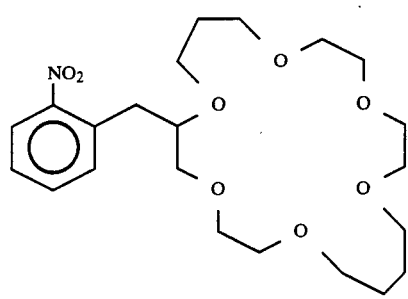
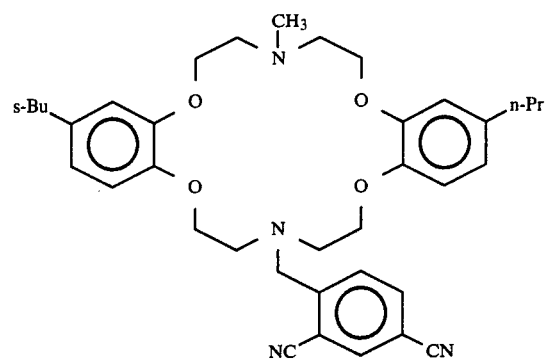
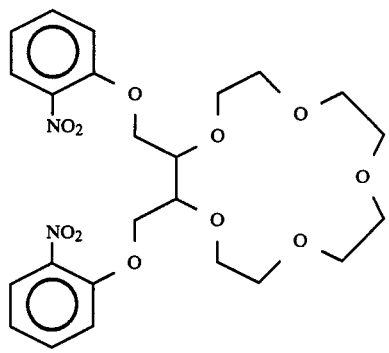
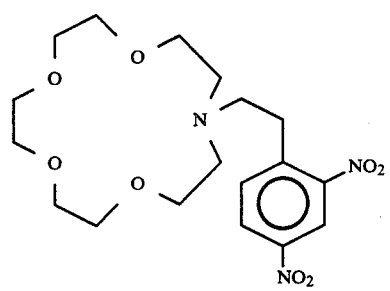
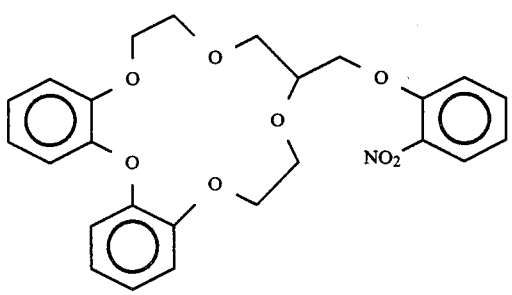
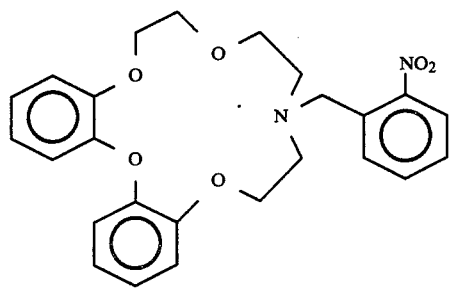
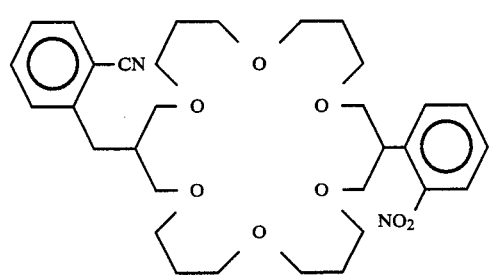
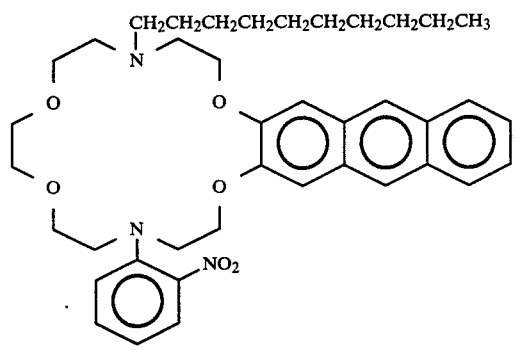

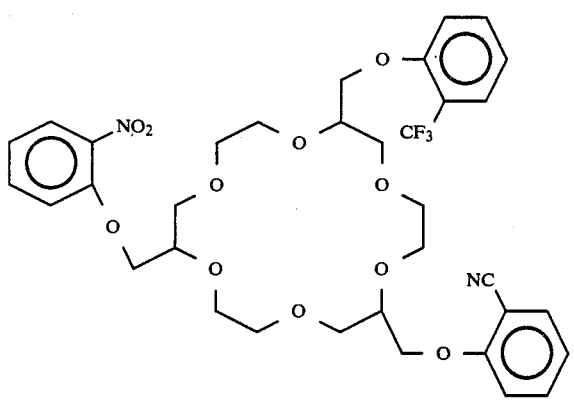
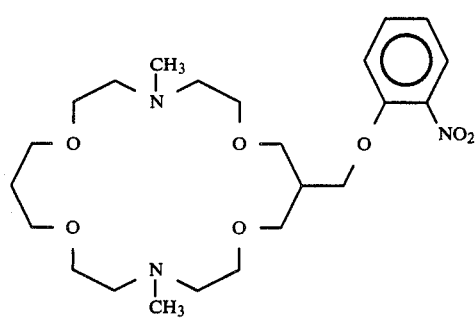
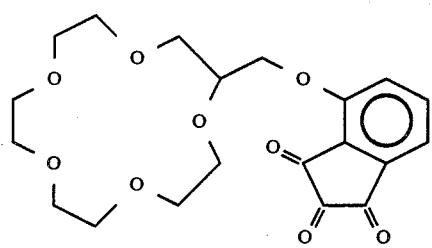
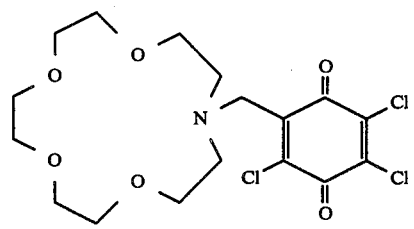
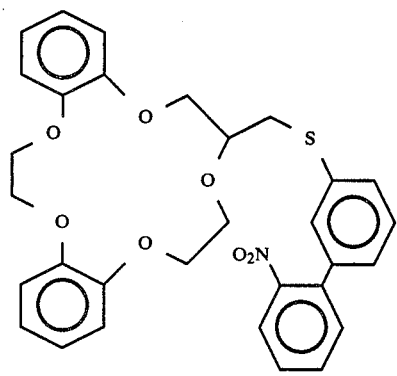
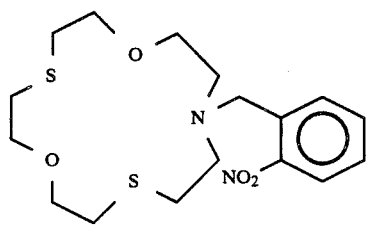
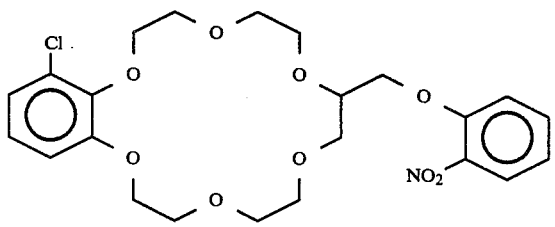
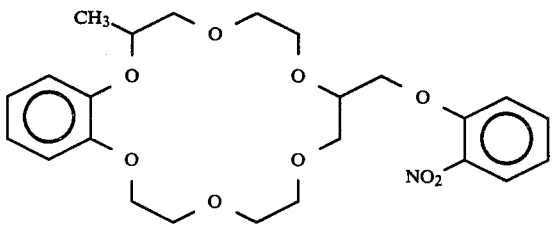
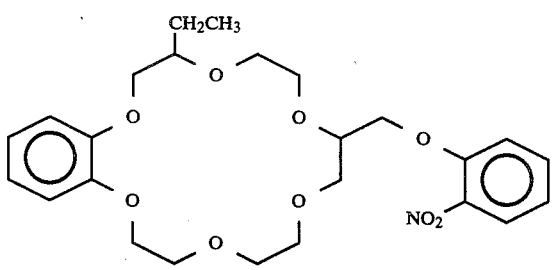
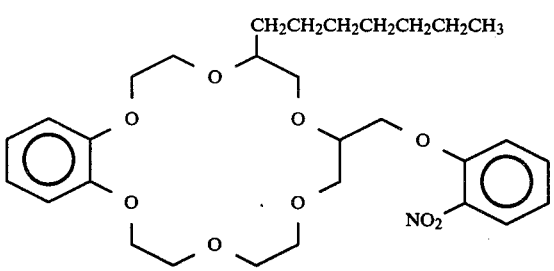

-continued
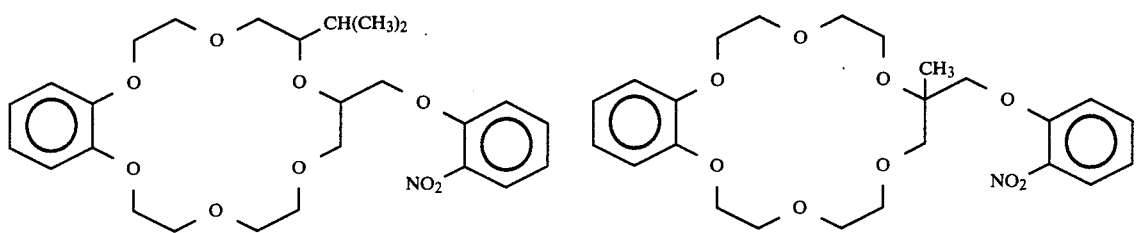
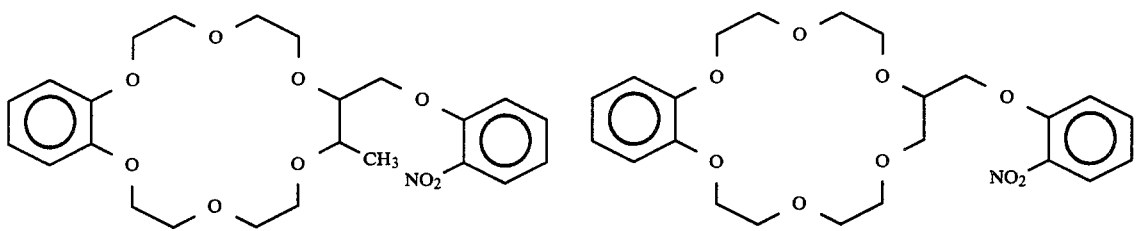
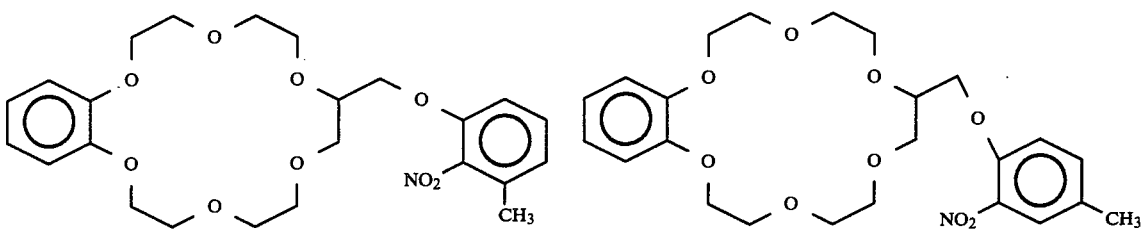
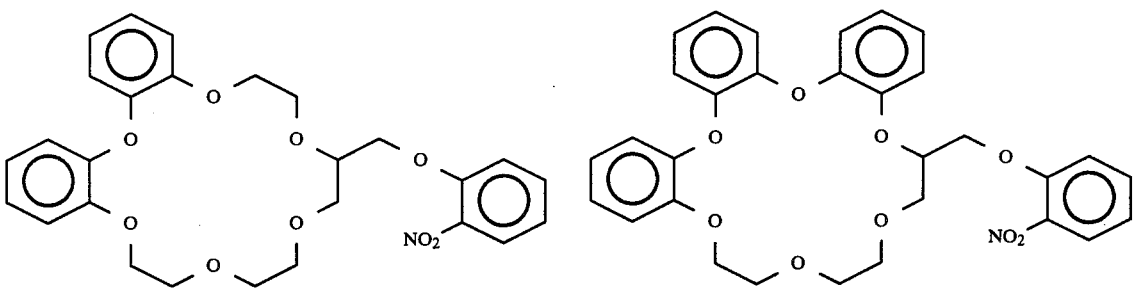
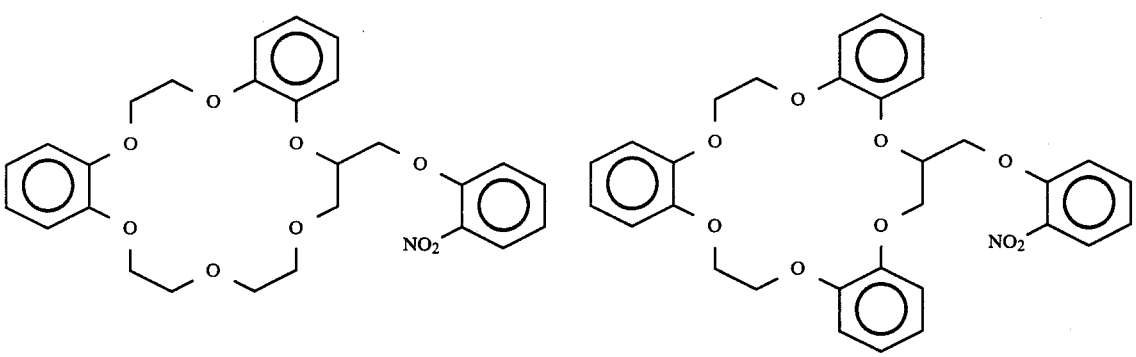

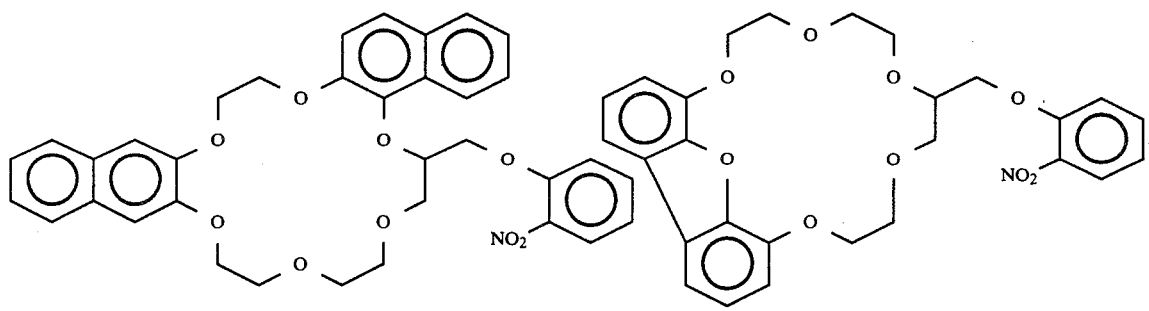
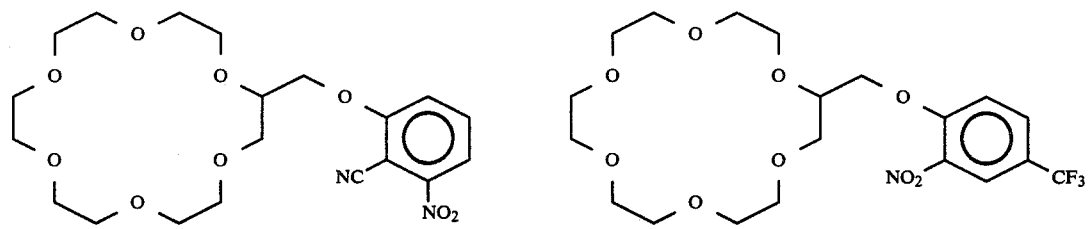
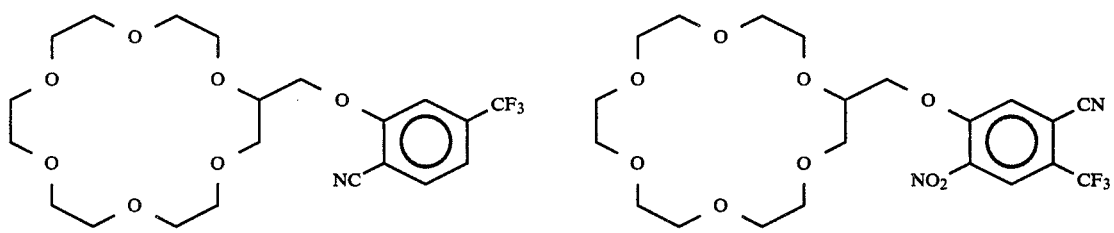
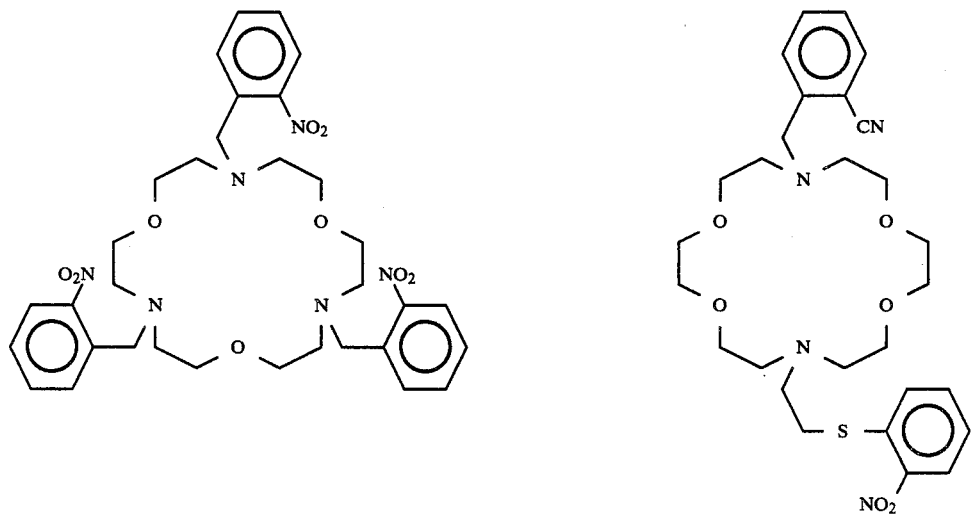
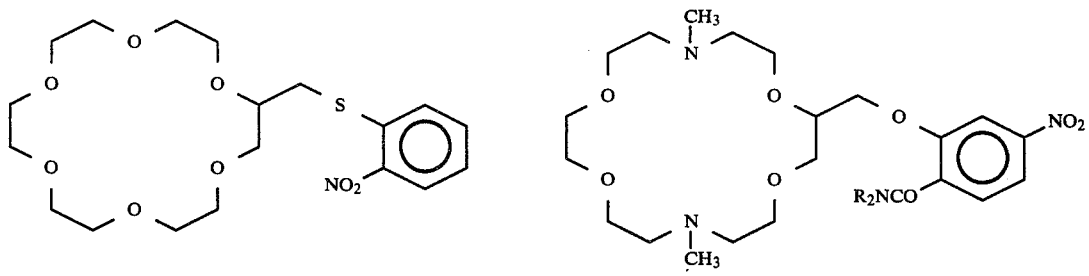

17
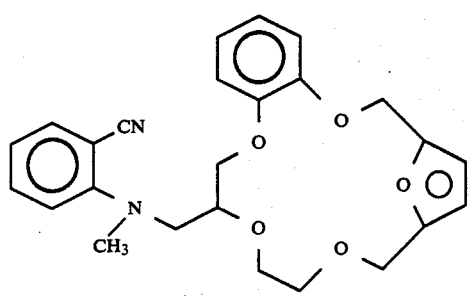
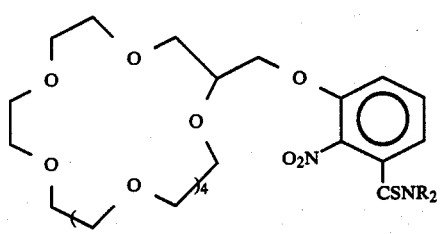
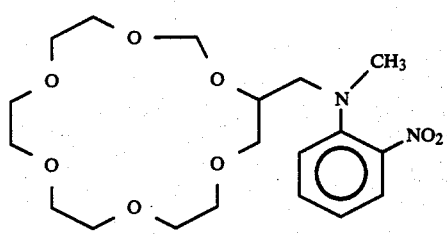
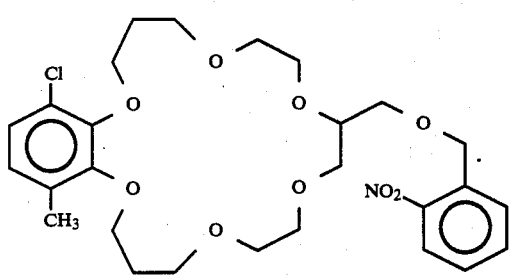
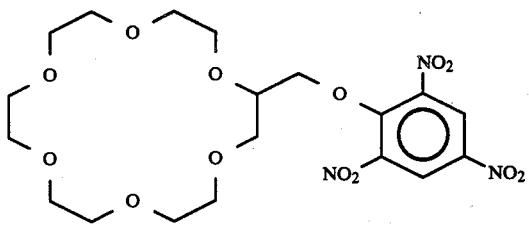
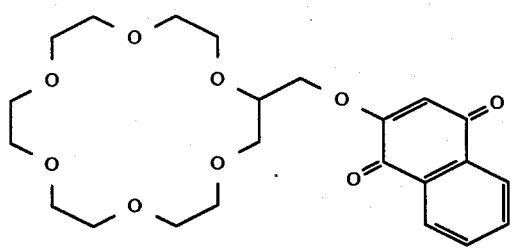
18
-continued
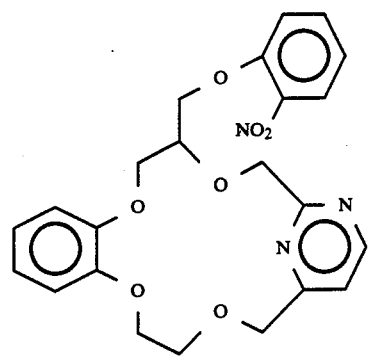
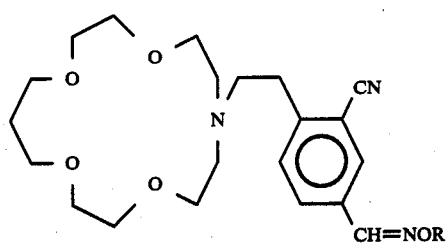
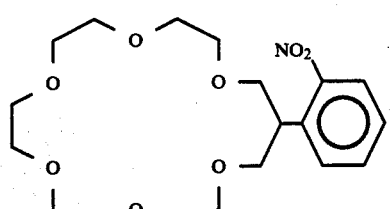
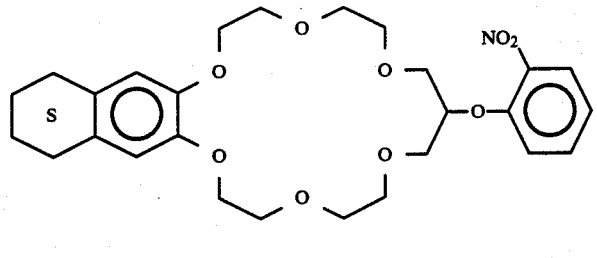
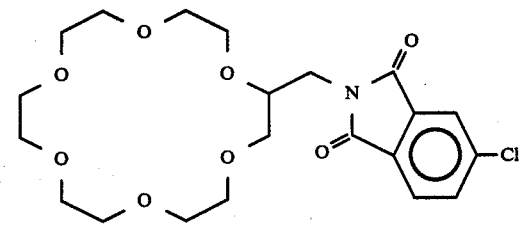
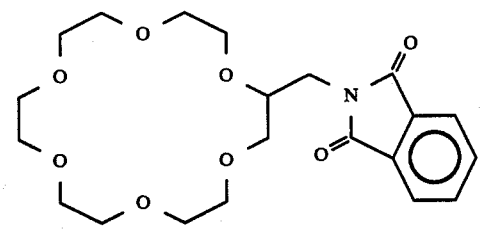

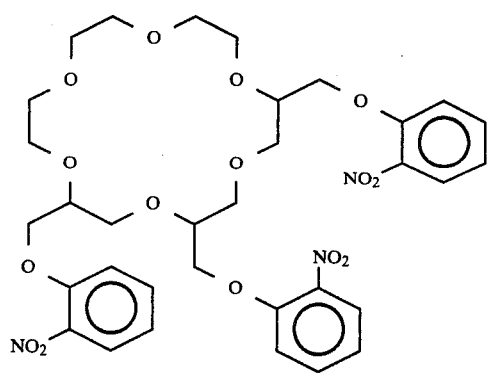
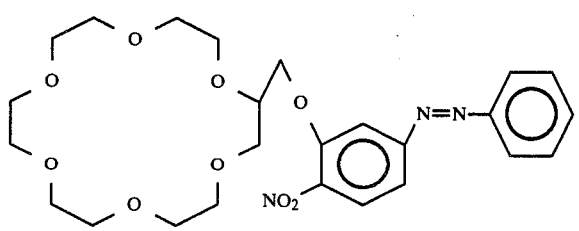
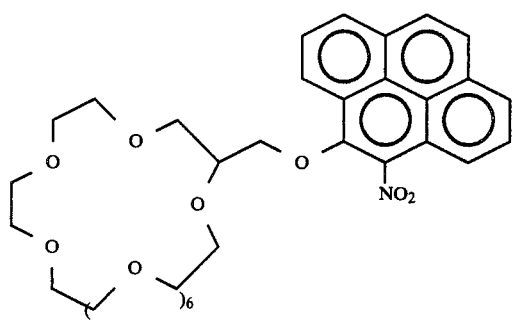
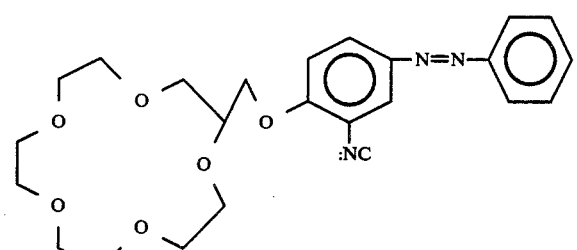
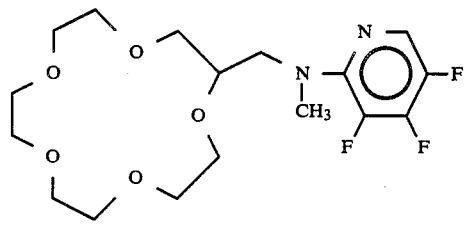
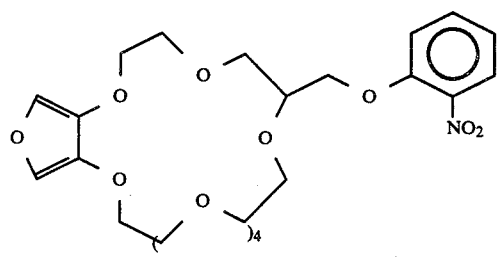
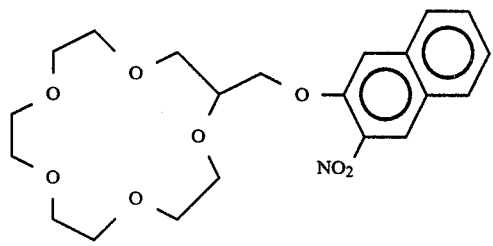
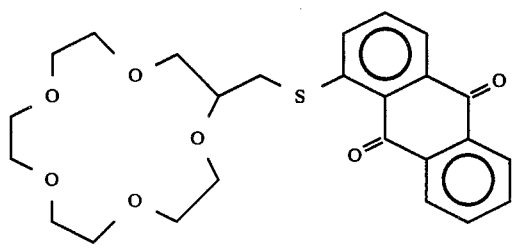
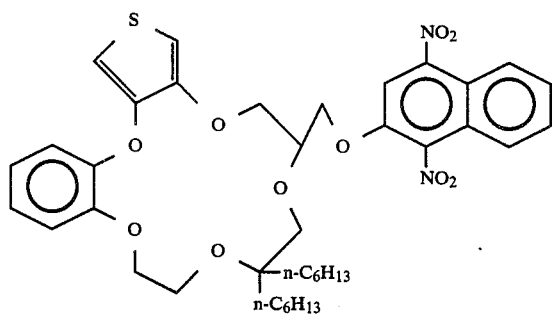
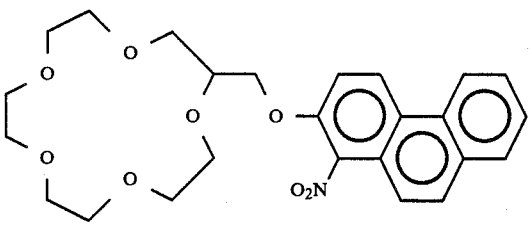

-continued
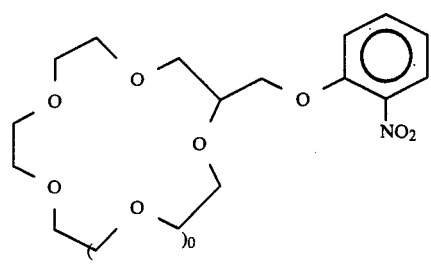
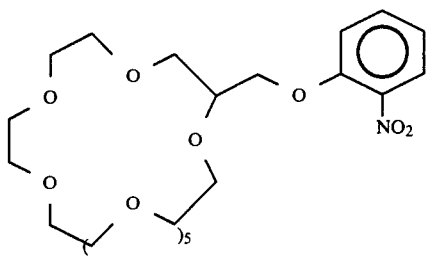
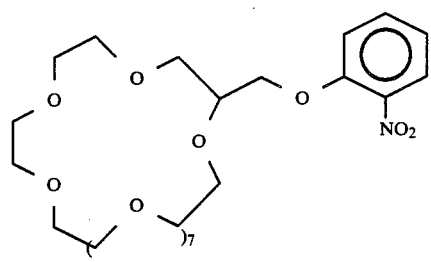
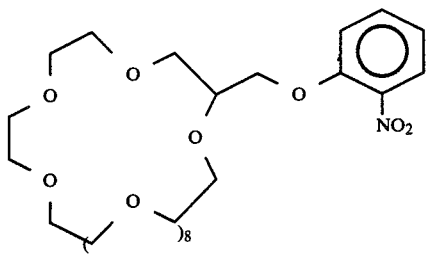
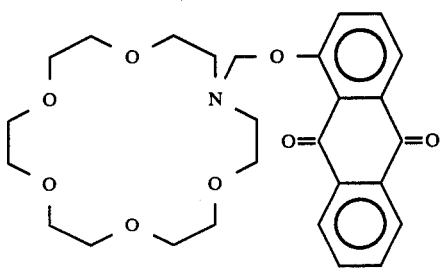
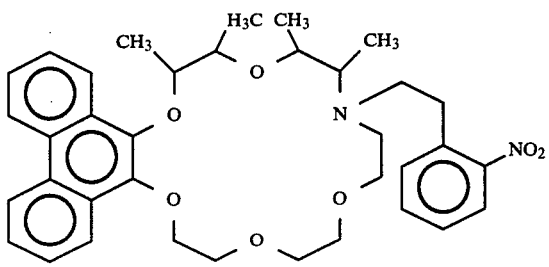
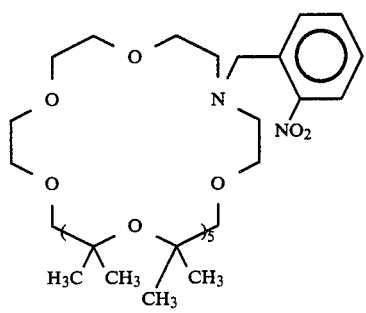
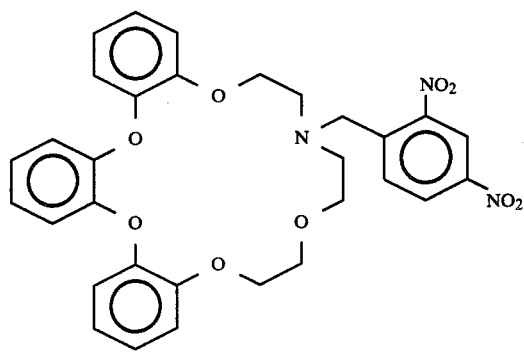
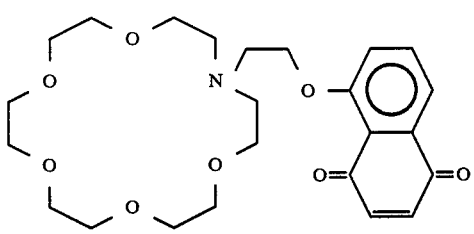
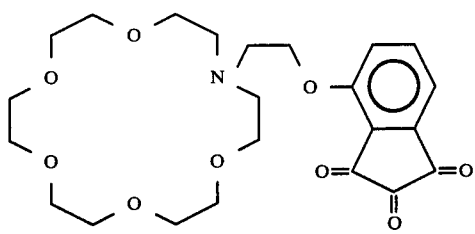

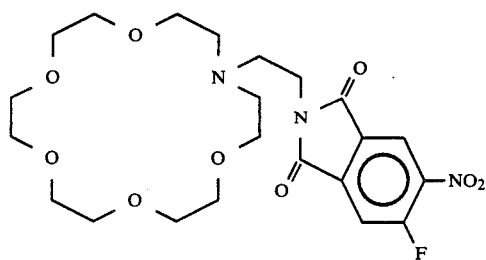
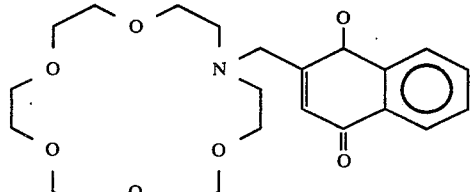
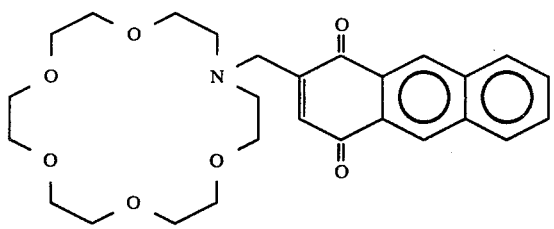
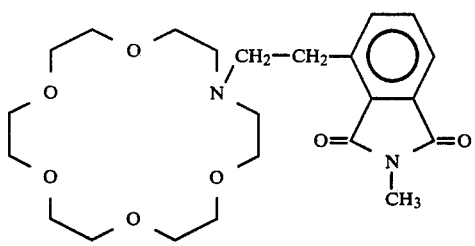
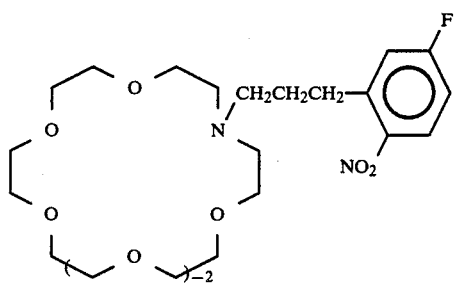
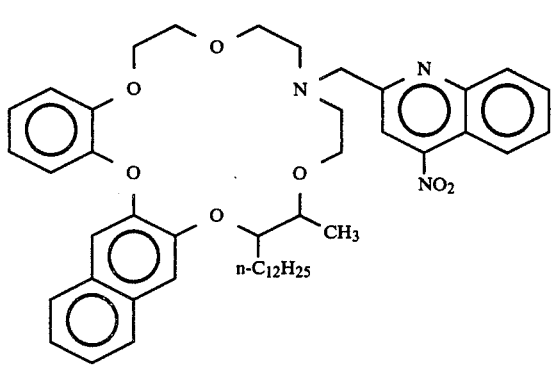

The compounds relevant to this invention include both carbon-pivot and nitrogen-pivot structures wherein the pivot is the point of attachment of the pendant group to the heteromacrocycle and may be carbon or nitrogen. Additionally, a number of compounds with one or two eletrochemically reducible arms has been prepared showing clearly that more arms may be incorporated. That is, arms can be attached to all of the bonding sites available in the heteromacrocycle. Compounds having ring sizes from 12 to 36 members behave in the same fashion, and the choice of ring size in general is determined by properties of the cation one desires to bind.

Specifically, this invention relates to substituted heteromacrocyclic ring compounds having from 12-36 atoms in the ring selected from the elements C, N, O and S represented by the following formula and in which the atoms N, O and S must be separated by at least one carbon atom. The compounds may be represented by the formula:

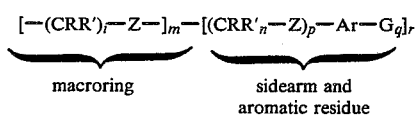

$$[-(CRR')_i-Z-]_m-[(CRR'_n-Z)_p-Ar-G_q]_r$$

macroring    sidearm and aromatic residue wherein

Ar is a carbocyclic aromatic or heteroaromatic residue selected from the group substituted benzene, naphthalene, anthracene, phenanthrene, fluoranthene, benzanthracene, chrysene, triphenylene, naphthacene, perylene, picene, pentacene, pentaphene, furan, thiophene, pyridine, pyridazine, pyrimidine, pyrazine, quinoline, isoquinoline, phthalazine, 1,8-naphthyridine, quinoxaline, quinazoline, cinnoline, carbazole, phenanthridine, acridine, phenanthroline or phenazine. Other electron deficient aromatic residues include, but are not restricted to, picryl, picramyl, phthalimidoyl, biphenyl and fused, aromatic dervatives thereof. The aforenamed aromatic or heteroaromatic residues must meet two qualifications to be the subject of the instant invention. First, they must be reducible at a potential below 2.0 V vs. SCE. Second, they must be substituted by or contain within the aromatic ring structure a group or heteroatom containing lone pair electrons which can serve as a donor to a ring-bound cation like group G, see below, or other uncharged Lewis basic residues. Examples of such groups are ethers (like —OCH$_3$ or —OC$_6$H$_5$); thioethers (like —SCH$_2$CH$_3$ or —SCH$_2$C$_6$H$_5$; F, Cl, or Br); amino (—NH$_2$); dialkylamino (—NRR'); nitroso (—N=O); nitro (—NO$_2$); cyano (—CN); trihalomethyl (—CX$_3$ where X may be F, Cl or Br in any combination); carbonyl oxygen as part of an aldehyde, ketone, quinone, ester, amide, urea or carbamate; thiocarbonyl sulfur as part of a thioaldehyde, thioketone, thioester, thioamide, thiourea or thiocarbamate; or other stable, Lewis basic donor group;

G is an electron attracting substituent on the aromatic residue selected from F, Cl or Br; nitroso (—N=O); nitro (—NO$_2$); cyano (—CN); trihalomethyl (—CX$_3$ where X may be F, Cl or Br in any combination); ester (—CO—OR, R=alkyl, aryl or substituted derivatives thereof, but not H), amide (—CO—NRR where R=alkyl, aryl or substituted derivatives thereof, but not H), thioester (—CS—OR where R=alkyl, aryl or substituted derivatives thereof but not H), thioamide (—CS—NRR', where R=alkyl, aryl or substituted derivatives thereof, but not H). The substituents may be present in any position and in any combination so that the net reduction potential of the aromatic residue is below 2.0 V vs. SCE. The aromatic residue may, itself, be electron deficient, as in the case of benzoquinone, naphthoquinone or pyridine In such cases, the donor group may be a heteroatom contained within the heterocyclic reducible aromatic residue;

R and R' are H or alkyl groups substituting C which contain from 1-12 carbon atoms and may form a portion of a substituted or unsubstituted carbocyclic aromatic residue such as 1,2-benzo-, 1,2-naphtho and the like, and the residues CRR' may or may not repeat throughout the macroring;

Z is an atom selected from the group N, O or S;

i is an integer from 1-5;

m is an integer such that the product $(i+1)(m)=12$ to 36 if the ring is symmetrical and if different lengths of carbon residues separate the heteroatoms, Z, within the macroring, the total of all carbon and Z atoms is 36 or less;

n is an integer from 1-5;

p is an integer such that the total number of atoms in the chain does not exceed 6;

q is an integer from 1 to one less than the total number of bonding sites available on Ar;

r is an integer from 1-4.

In the instant invention, binding and switching characteristics were determined by cyclic voltammetry. Cyclic voltammetry is an electroanalytical technique in which current is measured as a function of applied voltage in a cycle. The experiment is accomplished by first linearly increasing the potential until a peak is completed and then scanning linearly back to the starting point. The entire scan takes only a few seconds and is usually repeated several times.

At the beginning of the scan, reduction of the analyte (substrate) takes place. One or more electrons are added at a current which reaches a maximum at the peak. When the potential is reversed, the reduced species is reoxidized to its form at the start of the experiment. By observing the electrochemical behavior of the instant macrocyclic polyethers (lariat ethers) in the absence and presence of varying amounts of cations, the binding and switching characteristics of these compounds can be determined. It is also important to measure the cyclic voltammograms of closely related structures as well as macrocycles having no pendant groups and electron-deficient aromatics such as nitroanisole present in the same solution to show that only when all the component parts are present in the correct geometrical arrangement in the same molecule of the compositions herein are the switching properties observed.

EXPERIMENTAL DESCRIPTION OF THE INVENTION

The electrochemical experiments were performed under dry $N_2$ in MeCN containing 0.1 M $Bu_4NClO_4$. The supporting electrolyte was recrystallized twice from EtOAc and then dried in vacuo. A standard three-compartment cell, glassy carbon (0.35 cm$^2$ surface) and Pt wire electrodes were used. $E^o$ values are reported vs. an aq. Na$^+$-saturated calomel electrode (SSCE). The cyclic voltammetry measurements were done using a Bioanalytical Systems (model CV-1B) apparatus and recorded on a Hewlett-Packard Moseley 7035-B x-y recorder or with a Princeton Applied Research apparatus (models 173 and 176) and recorded on an H-P 7045A x-y recorder. The cyclic voltammograms for Compounds 1, 13, 24 and 26 are shown in FIGS. 1-4, respectively.

In all the examples the voltage was always measured against a sodium saturated calomel electrode or simply saturated calomel electrode, SCE.

EXAMPLE 1

Reduction of 2-(Nitrophenoxy)methyl-15-crown-5 (See FIG. 1)

A 2.0 mM solution of 2-(2-nitrophenoxy)methyl-15 crown-5 was prepared by mixing 18.6 mg (0.05 mmol) of the crown, 341.0 mg (1.0 mmol) of $Bu_4NClO_4$ and 25 mL of MeCN. A 12 mL aliquot was added to a standard three-compartment cell equipped with a magnetic stirrer and a dry $N_2$ inlet. After 0.25 h of $N_2$-purging and stirring, a cyclic voltammogram was recorded for the unstirred solution. The potential scan was initiated at 0 V and switched at $-1.6$ V. All potentials are reported vs. an aq. Na$^+$ saturated, calomel electrode. A scan rate of 200 mV/sec and a current setting of 100 uA/V were used. A quasi-reversible, one electron redox couple at $-1.28$ V was observed (designated A in FIG. 1a). Anhydrous $NaClO_4$ (0.5 equiv.) was added to the electrochemical cell and the solution stirred until the salt dissolved. The voltammogram was recorded and a new redox couple (quasireversible) appeared at $-1.11$ V with the original couple remaining at $-0.28$ V. See FIG. 1b. When a full equiv. of Na$^+$ is added, the redox couple at $-1.28$ V disappears and only the couple at $-1.11$ V (see peak B in FIG. 1c) with an enhanced current is observed.

EXAMPLE 2

Preparation of 2-(2-Nitrophenoxy)methyl-15-crown-5—Compound 1

2-(2-Nitrophenoxy)methyl-15-crown-5, 1, was prepared by treating the anion [NaH, Tetrahydrofuran (THF)] of 2-hydroxymethyl-15-crown-5, Compound 6, with 1 equiv. 1-chloro-2-nitrobenzene (25° C., 4 h). See prior art Reference 1(a) supra. The crown was a pale yellow oil isolated (55%) by chromatography over alumina. $^1$H-NMR (CDCl$_3$, PPM) 3.9 (m, 21H), 6.9-8.1 (m, 4H); Anal: calcd for $C_{17}H_{25}NO_8$: C, 54.98; H, 6.78; N, 3.77; found: C, 54.62; H, 6.91, N, 3.78.

EXAMPLE 3

Preparation of 2-(2-Nitrophenoxy)methyl-18-crown-6—Compound 2

Sodium hydride (0.36 g, 15 mmol) was washed with hexane (3×25 mL) to remove the oil and THF (20 mL) was added. A solution of 2-hydroxymethyl-18-crown-6 (2.0 g, 6.79 mmol) in the THF (15 mL) was added dropwise during 3 min. After stirring for 15 min., 1-fluoro-2-nitrobenzene (0.96 g, 6.8 mmol) in THF (10 mL) was added in a stream. The resulting mixture was stirred at room temperature for 1 hour and then at reflux overnight. The reaction mixture was cooled, filtered and the solvent was evaporated in vacuo. The residue was chromatographed (Al$_2$O$_3$, 0–10% 2-propanol/hexane. The compound crystallized in the eluent. It was recrystallized from 2% 2-propanol in hexane (1 g/15 mL solvent) to give pale yellow crystals (0.8 g, 28%), mp 66°–67° C. $^1$H-NMR: 6.8–8.0 (m, 4H), 3.7 (m, 25H). $^{13}$C-NMR: 152.46, 144.31, 133.75, 125.27, 120.22, 114.82, 78.30, 77.39, 77.04, 75.76, 71.08, 70.71, 70.34, 70.20. IR (nujol): 3000, 2900, 1425, 1100 cm$^{-1}$. Anal. Calcd for C$_{19}$H$_{29}$NO$_9$: C, 54.93; H, 7.03; N, 3.37. Found: C, 55.07; H, 7.22; N, 3.23.

EXAMPLE 4

Preparation of 2-(2-Nitrophenoxy)methyl-21-crown-7—Compound 3

Sodium hydride (34 mg, 1.4 mmol) was slurried with THF (25 mL). This mixture was treated with a solution of 2-hydroxymethyl-21-crown-7 (prepared in Example 12, below, 0.46 g, 1.4 mmol) in THF (10 mL and stirred until H$_2$ evolution ceased. 1-Chloro-2-nitrobenzene (0.22 g, 1.4 mmol) in THF (10 mL) was added in a stream. The mixture was stirred overnight at ambient temperature, filtered, the solvent evaporated and the remaining oil chromatographed (alumina, 5% ether/hexane, then by 5% i-PrOH/hexane) to give Compound 3, as a pale yellow oil: 0.26 g (40%); $^1$H-NMR (CDCl$_3$: 3.57–4.37 (m, 29H, sharp singlet at 3.73), 6.93–7.96 (m, 4H); IR (neat) 1605, 1525, 1350, 1110 (br), 745 cm$^{-1}$. Anal.: Calcd for C$_{21}$H$_{33}$NO$_{10}$: C, 54.89; H, 7.24; N, 3.05. Found: C, 54.85; H, 7.50; N, 3.05.

EXAMPLE 5

Preparation of 2-(4-Nitrophenoxy)methyl-15-crown-5—Compound 4

2-(4-Nitrophenoxy)methyl-15-crown-5, Compound 4, was prepared in analogy to Compound 1 (Example 2) and isolated (bp 175° C./0.1 mm) as a yellow oil in 74% yield. $^1$H-NMR (CDCl$_3$, PPM) 3.7 (m, 21H), 7.0–8.2 (dd, 4H); Anal: (isomer of Compound 1), found: C, 54.99; H, 6.95; N, 3.90.

EXAMPLE 6

Preparation of 2-(4-Nitrophenoxy)methyl-18-crown-6—Compound 5

The procedure for the preparation of this compound is identical to that for Compound 2 (shown in Example 3) except that 1-fluoro-4-nitrobenzene was used instead of 1-fluoro-2-nitrobenzene. The column chromatography afforded a viscous yellow oil, which was further purified by Kugelrohr distillation (bp 176°–180° C., 0.01 torr); yield: 1.64 g, (58.6%). The compound solidified on standing in the refrigerator and was crystallized from 2% 2-propanol/hexane (mp 55° C.). $^1$H-NMR: 6.8–8.4 (d, 4H), 3.7 (m, 25H). IR (neat): 3080, 2900, 1600, 1500, 1450, 1350, 1250, 1100 (br) cm$^{-1}$. $^{13}$C-NMR 162.54, 141.07, 125.67, 114.65, 78.23, 77.52, 76.98, 75.96, 71.21, 70.80, 70.23, 69.25. Anal calcd for C$_{19}$H$_{29}$NO$_9$: C, 54.93; H, 7.03; N, 3.37. Found: C, 55.02; H, 7.16; H, 3.31.

EXAMPLE 7

Preparation of 2-(2,4-Dinitrophenoxy)methyl-15-crown-5—Compound 7

A slurry of NaH (0.48 g, 20 mmol) in THF (30 mL) was treated with a THF (20 mL) solution of 2-hydroxymethyl-15-crown-5 (5.00 g, 20 mmol) and stirred until H$_2$ evolution ceased. A solution of 1-chloro-2,4-dinitrobenzene (4.05 g, 40 mmol) in THF (10 mL) was added in a stream. The mixture was stirred overnight at ambient temperature, then filtered, the solvent evaporated and the residue chromatographed (alumina, 0–10% i-PrOH/hexane) to afford Compound 7, as a viscous pale yellow oil: 2.41 g (29%); NMR (CDCl$_3$) 3.56–4.43 (m, 21H, singlet at 3.67), 7.40 (d, 1H, J=10 Hz), 8.53 (dd, 1H, J=10, 2 Hz), 8.87 (d, 1H, J=2 Hz); IR (neat) 1605, 1525, 1345, 1125 (br), 830 cm. Anal. Calcd for C$_{17}$H$_{24}$N$_2$O$_{10}$: C, 49.04; H, 5.81; N, 6.73. Found: C, 49.22; H, 5.94; N, 6.69.

EXAMPLE 8

Preparation of 2-Methoxy-3'-nitrobiphenyl

Anisole (400 mL) and 3-nitrobenzenediazonium tetrafluoroborate (54.5 g, 0.23 mol) were placed in a 1-L flask and stirred mechanically. Potassium acetate (49.0 g, 0.5 mol) was added in one portion. The mixture turned red and warmed slightly. Stirring was continued 12 h., then the solution was filtered and the anisole evaporated in vacuo. Column chromatography of the residue (alumina, 0–10% ether/hexane, first yellow band) and recrystallization (95% EtOH) provided pure 2-methoxy-3'-nitrobiphenyl: 18 g (35%); mp 68°–69° C.

EXAMPLE 9

2-Hydroxy-3'-nitrobiphenyl

2-Methoxy-3'-nitrobiphenyl (9.00 g, 3.9 mmol) was heated at reflux with HOAc (50 mL) and 48% HBr (50 mL) for 8 h. The solution was then concentrated in vacuo, poured into ice-cold H$_2$O (300 mL) and extracted with CH$_2$Cl$_2$. The organic layer was dried, evaporated and recrystallized (50% aq MeOH) to afford 2-hydroxy-3'-nitrobiphenyl as yellow needles; 6.12 g (73%); mp 99.5°–100° C.

EXAMPLE 10

Preparation of (15-Crown-5)-methyl 4-Toluenesulfonate—Compound A

A 10 mL flask was charged with 4-toluenesulfonyl chloride (0.76 g, 4.0 mmol) and pyridine (1.0 mL) and cooled in an ice bath. A solution of 2-hydroxymethyl-15-crown-5 (see prior art reference 1a, supra) (1.0 g, 4.0 mmol) in pyridine (1 mL) was added dropwise (5 min.) and the mixture was stirred 1 h. Water (10 mL) was added and the mixture was extracted with CH$_2$Cl$_2$ (3×15 mL). The combined extracts were washed with ice-cold 6N HCl (3×10 mL), brine (10 mL) and dried. (15-Crown-5)-methyl 4-toluenesulfonate, Compound A, (1.4 g, 87%) was isolated as a pale yellow oil: $^1$H-NMR: 2.45 (s, 3H), 3.64 (m, 19H), 4.15 (m, 2H), 7.7 (q, 4H); $^{13}$C-NMR: 21.57, 69.86, 70.30, 70.68, 71.03, 77.00, 127.74, 129.57, 132.87, 144.46; IR 2850, 1360, 1120, 700 cm$^{-1}$. Anal.: Calcd for C$_{18}$H$_{28}$O$_8$S: C, 53.45; H, 6.98. Found: C, 53.59; H, 7.11.

EXAMPLE 11

Preparation of 2-[2-(3-Nitrophenyl)phenoxymethyl]-15-crown-5—Compound 10

Anhydrous K$_2$CO$_3$ (0.54 g, 2.9 mmol) was added to a mixture of (15-crown-5)methyl 4-toluenesulfonate (1.28 g, 2.6 mmol) and 2-hydroxy-3'-nitrobiphenyl (0.56 g, 2.6 mmol) in DMF (15 mL). The mixture was magnetically stirred and heated at 50° C. overnight. After cooling, the solution was poured into H$_2$O (50 mL) and the mixture was extracted with ether (2×25 mL). The combined extracts were dried. The residue after evaporation of the solvent was chromatographed (alumina, 0–5% 2-propanol/hexane) to afford Compound 10 as a viscous yellow oil: 0.71 g (61%); $^1$H-NMR: 3.50–4.23 (m, 21H, sharp singlet at 3.73), 6.90–8.57 (m, 8H); $^{13}$C-NMR: 69.04, 70.35, 77.81, 112.32, 121.00, 121.38, 124.41, 127.96, 128.49, 129.65, 130.30, 135.43, 139.99, 147.73, 155.44; IR 1520, 1345, 1110 (br), 720 cm$^{-1}$. Anal. Calcd for $C_{23}H_{29}NO_8$: C, 61.80; H, 6.43; N, 3.13. found: C, 61.44; H, 6.77; N, 3.11.

EXAMPLE 12

Sequence for the Preparation of 2-Hydroxymethyl-21-crown-7—Compound B

Ethylene glycol monobenzyl ether (30 g, 0.20 mol) was added to NaH (10.4 g, 0.20 mol) suspended in THF (150 mL) and heated at reflux for 5 h. After an additional 0.5 h., tetraethylene glycol ditosylate (50.2 g, 0.10 mol) in THF (100 mL) was added over a 1 h. period. The mixture was stirred for 24 h. at reflux, then cooled, filtered and the THF evaporated. The residue was taken up in $CH_2Cl_2$ (150 mL) and washed with $H_2O$ and brine, then dried. The crude hexaethylene glycol dibenzyl ether, C, was Kugelrohr distilled, affording the pure C (31.6 g, 69%) as a pale yellow oil: bp 198°–250° C. (0.03 torr); $^1$H-NMR 3.66 (s, 24H), 4.54 (s, 4H), 7.32 (s, 10H); IR 2860, 1600, 1490, 1450, 1350, 1290, 1120, 700 cm$^{-1}$. Anal. Calcd for $C_{26}H_{38}O_7$: C, 67.51; H, 8.28. Found: C, 67.80; H, 8.59.

EXAMPLE 13

Dibenzyl ether, Compound C (31.0 g, 0.067 mol), was deprotected by catalytic hydrogenolysis (60 psi) in the presence of 10% Pd/C catalyst, (100 mg) and concentrated HCl (1 mL) to afford hexaethylene glycol (17.3 g, 91%) as a nearly colorless oil: bp 164°–168° C. (0.05 torr); $^1$H-NMR 3.0 (broad s, 2H), 3.67 (s, 24H).

EXAMPLE 14

Hexaethylene glycol was converted into the corresponding ditosylate, Compound D, using experimental conditions reported in prior art Reference 1(c) for the corresponding pentaethylene glycol.

EXAMPLE 15

Ditosylate, Compound D (30 g, 0.066 mol), was then cyclized with 3-benzyloxy-1,2-propanediol (12.0 g, 0.066 mol) in the presence of NaH (6.97 g, 0.145 mol) in THF (500 mL). Crude benzyloxymethyl-21-crown-7, Compound E was chromatographed (alumina, 0–2% 2-propanol/hexane) to afford a yellow oil (8.1 g). This was further purified by Kugelrohr distillation, and the pure benzyloxymethyl-21-crown-7 (4.8 g, 17%) was isolated as a pale yellow oil: bp 186°–188° C. (0.04 torr); $^1$H-NMR 3.34 (m, 29H), 4.51 (s, 2H), 7.40 (s, 5H); IR 2860, 1450, 1120, 735 cm$^{-1}$. Anal. Calcd for $C_{22}H_{26}O_8$ C, 61.66; H, 8.47. Found: C, 61.84; H, 8.63.

EXAMPLE 16

Hydrogenolysis of benzyloxymethyl-21-crown-7 (4.77 g, 0.011 mol) in the presence of 10% Pd/C (100 mg) in absolute ethanol gave 2-hydroxymethyl-21-crown-7, Compound B, (3.52 g, 94%) as a colorless oil after Kugelrohr distillation: bp 148°–152° C. (0.03 torr); $^{13}$C-NMR 62.17, 69.54, 70.38, 70.76, 71.26, 79.39; IR 2860, 1450, 1110, 840 cm$^{-1}$. Anal. Calcd for $C_{15}H_{30}O_8$: C, 53.24; H, 8.94. Found: C, 53.27; H, 9.20.

EXAMPLE 17

Preparation of (21-Crown-7)methyl 4-toluenesulfonate—Compound F

A solution of 2-hydroxymethyl-21-crown-7 (2.00 g, 5.9 mmol) in pyridine (5 mL) was added dropwise to a stirred mixture of 4-toluenesulfonyl chloride (1.25 g, 6.6 mmol) and pyridine (5 mL) at ca. 0° C. After stirring 1 h, $H_2O$ (10 mL) was added. This mixture was extracted with $CH_2Cl_2$ (30 mL). The organic phase was then washed with ice-cold 6N HCl (15 mL) and dried. Evaporation of the $CH_2Cl_2$ left the tosylate (2.45 g, 84%) as a nearly colorless oil: $^1$H-NMR 2.37 (s, 3H), 3.54 (m, 27H), 4.00 (m, 2H), 7,60 (q, 4H); $^{13}$C-NMR 21.48, 69.51, 69.83, 69.98, 70.53, 70.79, 76.59, 127.65, 129.49, 132.75, 144.40; IR 2870, 1360, 1175, 1120, 785 cm$^{-1}$. Anal. Calcd for $C_{22}H_{36}O_{10}S$: C, 53.64; H, 7.37. Found: C, 53.51; H, 7.41.

EXAMPLE 18

Preparation of 2-[2-(3-Nitrophenyl)phenoxymethyl]-21-crown-7—Compound 12

To a stirred mixture of (21-crown-7)methyl 4-toluenesulfonate (0.96 g, 1.9 mmol) and 2-hydroxy-3'-nitrobiphenyl (0.42 g, 1.9 mmol) in DMF (10 mL) was added anhydrous $K_2CO_3$ (0.41 g., 3 mmol). This mixture was stirred 8 h at 50° C., then poured into $H_2O$ (30 mL), extracted with ether and dried. Column chromatography of the oil (alumina, 0–5% 2-propanol/hexane) and evaporation of the solvent provided Compound 12 as a thick yellow oil: 0.54 g (53%); $^1$H-NMR 3.66–4.23 (m, 29H, tall peak at 3.70), 6.90–8.53 (m, 8H); $^{13}$C-NMR 68.75, 70.79, 77.99, 112.53, 121.18, 121.53, 124.53, 128.12, 128.61, 129.77, 130.42, 135.57, 140.11, $C_{27}H_{37}NO_{10}$; C, 60.55, H, 6.96, N, 2.61. Found: C, 60.32; H, 6.89; N, 2.72.

EXAMPLE 19

N-Nitrobenzylation of Monoaza-15-crown-5

Monoaza-15-crown-5, obtained by hydrogenolysis of N-benzylmonoaza-15-crown-5 (9 mmol) as described in prior art Reference 1(c), $Na_2CO_3$ (18 mmol), MeCN (30 mL) and either 2- or 4-nitrobenzyl bromide (9 mmol) were heated at reflux for 24 h. The reaction mixture was cooled, filtered, the solvent evaporated and the residue dissolved in $CHCl_3$ (20 mL), cooled, filtered and the solvent evaporated. This residue was then purified as described below.

EXAMPLE 20

Preparation of N-2-Nitrobenzylmonoaza-15-crown-5—Compound 13

Compound 13 was isolated (35%) as a yellow oil after chromatography (200 g, $Al_2O_3$, 2% 2-PrOH/hexanes) and Kugelrohr distillation (156°/0.05 torr). $^1$H-NMR: 2.75 (t, 4H); 3.60 (m, 16H); 3.95 (s, 2H); 7,50 (m, 4H). IR (neat): 2860, 1530, 1450, 1355, 1300, 1125, 935, 740 cm$^{-1}$. Anal. Calcd for $C_{17}H_{26}N_2O_6$: C, 57.61; H, 7.39; N, 7.90; Found: C, 57.81; H, 7.58; N, 8.09.

EXAMPLE 21

Preparation of N-4-Nitrobenzylmonoaza-15-crown-5—Compound 16

Compound 16 was isolated (22%) as a yellow oil after chromatography over $Al_2O_3$ (200 g, 2% 2-PrOH/hexanes), then Kieselgel 60 Silica (300 g, 18:1 $CHCl_3$/MeOH) and finally Chromatotron chromatography (0.75 g partially purified Compound 16 in 10 mL $CHCl_3$ applied to a 4 mm rotating silica plate, eluted with $CHCl_3$, collecting 5 mL fractions). Compound 16 solidified on standing for 500 h. $^1$H-NMR: 2.75 (t, 4H); 3.65 (m, 18H); 7.85 (dd, 4H). IR (Nujol): 2900, 1600, 1520, 1350, 1310, 1260, 1125, 860, 750 cm$^{-1}$. Anal. (isomer of Compound 13). Found: C, 57.38; H, 7.58; N, 7.80.

EXAMPLE 22

Preparation of 2-(2-Cyanophenoxymethyl)-15-crown-5—Compound 19

Sodium hydride (50% in mineral oil; 0.26 g, 5.4 mmole) was washed with hexanes and suspended in dry THF (15 mL). A solution of 2-cyanophenol (0.64 g, 5.4 mmole) in THF (8 mL) was added dropwise during 10 min while stirring under nitrogen. Next, a solution of hydroxymethyl-15-crown-5 tosylate (2.0 g, 4.9 mmole) in THF (8 mL) was added dropwise over 20 min. The reaction was stirred at reflux for 18 h. After cooling, water was added dropwise to the reaction mixture until the evolution of gasses ceased. The solvent was removed in vacuo and CHCl$_3$ was added. The organic phase was washed with H$_2$O, dried [MgSO$_4$] and concentrated. The resulting oil was Kugelrohr distilled [bp 185°–187° C./0.2 torr] to yield Compound 19 [1.2 g, 86%] as a yellow oil which proved to be greater than 95% pure by gas chromatographic analysis. $^1$H-NMR (CDCl$_3$, PPM, delta): 3.5–4.2 (m, 21H); 6.8–7.7 (m, 4H). IR (neat): 2220, 1600, 1580, 1490, 1450, 1350, 1290, 1240, 1130, 760 cm$^{-1}$. Anal: Calcd for C$_{18}$H$_{35}$NO$_6$; N, 3.99%. Found: N, 3.88%.

EXAMPLE 23

Synthesis of N,N'-Bis(2-nitrobenzyl)-1,10-diaza-18-crown-6—Compound 23

A stirred solution containing 1.0 g (3.8 mmol) of 1,10-diaza-18-crown-6, 1.3 g (7.8 mmol) of 2-nitrobenzyl chloride, 2.0 g (19.0 mmol) of Na$_2$CO$_3$ and 20 mL of CH$_3$CN was heated at reflux for 16 hrs. The reaction was cooled and concentrated, and the oily residue is added to 20 mL of CHCl$_3$. The organic phase was washed with 20 mL of distilled water, dried over anhydrous MgSO$_4$ and concentrated in vacuo. Upon standing at 0° C., the oily residue crystallized. After two recrystallizations (EtOH followed by 5% hexanes-/EtOH), 1.8 g (90%) of a yellow solid (mp 78°–79° C.) was obtained: $^1$H-NMR (CDCl$_3$): 2.80 (t, 8H, NCH$_2$), 3.60 (t and s, 16H, OCH$_2$), 4.00 (s, 4H, benzyl), 7.33–7.93 (m, 8H, aromatic); IR (KBr) 2860, 1520, 1360, 1350, 1140, 1130, 730 cm$^{-1}$; Anal. Calcd for C$_{26}$H$_{36}$N$_4$O$_8$: C, 58.62; H, 6.83; N, 10.52%. Found: C, 58.59; H, 7.02; N, 10.66%.

2-Nitroanisole, commercially available from Eastman Organic Chemicals, will be referred to herein as Compound 24. 4-Nitroanisole, commercially available from Eastman Organic Chemicals, will be referred to herein as Compound 25. 2-Nitrotoluene, commercially available from Eastman Organic Chemicals, will be referred to herein as Compound 26. 4-Nitrotoluene, commercially available from Eastman Organic Chemicals, was recrystallized from 90% EtOH and dried in vacuo and will be referred to herein as Compound 27.

The cyclic voltammograms (cvs) for Compound 1 and 2-nitroanisole (Compound 24) in the presence and absence of Na$^+$ are shown in FIGS. 1 and 2. The data for Compounds 1, 24, 4 and 4-nitroanisole (Compound 25) are summarized in TABLE 1. The quasi-reversible, one-electron redox couples for Compounds 1 and 24 (FIGS. 1 and 3, respectively) exhibit virtually identical E$^{o\prime}$ values. This shows that both CH$_3$O— and crown-CH$_2$O— have a similar effect on the nitroaromatic nucleus. The nitroanisole is therefore a suitable model for the chemistry of the crown compound. When NaClO$_4$ (0.5 equiv.) is added to solutions of Compounds 1 or 24, a new redox couple (quasi-reversible for Compound 1, see peak B in FIG. 1b; irreversible for couple 24, see peak D in FIG. 3) appears in each case. Couple A disappears when a full equiv. of Na$^+$ is added to Compound 1 (see FIG. 1c) and only couple B is observed, with an enhanced current. This means that a new, cation-bound species is present in the solution. The oxidation peak of couple D moves to more positive potential when 1 equiv. Na$^+$ is added to Compound 24 (see FIG. 3c), the reduction potential does not change, and peak C in FIG. 3c is not dissipated. In the absence of Na$^+$, the single redox couples observed for Compounds 4 and 25 are nearly identical (see TABLE 1) since the reducible residues are essentially the same. The similarity continues when 0.5 equiv. of Na$^+$ is present in solutions of Compounds 4 or 25. No new redox couple is observed in either case although additional Na$^+$ increases irreversibility (see TABLE 1), evidencing that the donor group is in a position suitable for steric interaction between it and ring-bound sodium cation or switching will not be observed.

The results clearly show an intramolecular interaction between the macroring-bound cation and the reduced electron-deficient aromatic sidearm of Compound 1. The intramolecularity of this interaction is clear from two lines of evidence. First, Compound 4, which has all the structural elements of Compound 1, behaves differently because the nitro group is inappropriately situated. Second, the significant intermolecular interaction between Na$^+$ and Compound 24$^-$, which leads to electrochemically irreversible behavior, contrasts appreciably with the weaker interaction observed between Na$^+$ and Compound 1$^-$ (compare FIGS. 1 and 3). The latter process is quasi-reversible, indicating that the electrode processes for couple B (FIG. 1) are kinetically fast. This is due to the macroring-bound Na$^+$ being readily available to intramolecularly ion-pair with the reduced electron-deficient aromatic sidearm.

The electrochemically enhanced binding constant, Ks, for Compound 1$^-$ with Na$^+$ can be assessed by a simple, thermochemical cycle since the E$^{o\prime}$ values are known and Ks$_{1\cdot Na+}$ has been measured by previously described methods as set out in prior art Reference 1. Redox couples A and B in FIG. 1 correspond to equations 2 and 1 respectively. The difference (eqn. 2−eqn. 1=eqn. 3) gives K$_{ee}$ for electron exchange between 1$^-$ and 1.Na$^+$

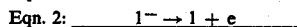
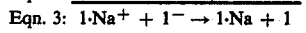

K$_{ee}$, when multiplied by Ks$_{(1\cdot Na+)}$, gives the stability constant for the Na$^+$·1$^-$ complex. From the E$^{o\prime}$ values, the electrochemically reduced ligand binds Na$^+$ 750 times more strongly than does the neutral ligand. Therefore, log Ks$_{1\cdot Na}$=6.33.

The electrochemical results observed when Na$^+$ is added to a solution of Compound 13 as shown in FIG. 2 are similar to the results for 2-(2-nitrophenoxy)methyl-15-crown-5, Compound 1, but the results are much more striking. In the present case, the initial redox couple for neutral Compound 13 is observed at −1.16V vs. SCE (see FIG. 3). When Na$^+$ is added to Compound 13, a new redox couple appears at −0.90 V, a 0.26 V displacement. The corresponding displacement in the C-pivot system (Compound 1, FIG. 1) was 0.17 V or substantially less than observed in the present case.

The clear relationship between the relative peak intensities of the respective couples for Compound 13 as the Na+ concentration is increased is shown in FIG. 3 and demonstrates that the new, quasi-reversible redox couple corresponds to the Na+-lariat ether complex. When 2-nitrotoluene (Compounds 26) is reduced in MeCN solution as described in Example 1 above, a quasireversible couple is observed at −1.17 V. As expected, this potential is almost identical to that of 2-nitrophenoxymethyl-15-crown-5 (Compound 1). When Na+ is added to Compound 26, a new redox couple is observed, but in this case the couple is quite irreversible (see FIG. 4). The current intensity of this new couple depends on the amount of Na+ present as it does with Compound 13.

There are two important differences observed between these two systems. First, the peak potentials of the new redox couple observed with Compound 26 are not much different from the original couple. This demonstrates a relatively weak interaction when Na+ interacts with the sidearm only (Compound 26) and no polyether ring is present. Second, the difference in reversibility of the new redox couple (Compound 13 compared to Compound 26) is due to the fact that Na+ is kinetically available to interact with the reduced electron-deficient aromatic sidearm when it is already bound by the macroring. This is not the case when the sidearm is not attached to a ring and the nitroaromatic must compete with solvent for Na+ cation. This is clear evidence for cooperative binding involving both the sidearm anion radical and macroring in Compound 13.

Confirmation of this intramolecular cooperativity is also obtained by comparing the 2- and 4-nitrophenyl lariat ethers (Compounds 13 and 16). In Compound 16, the nitro group is too remote to interact with a ring-bound cation; so no second redox couple is observed, even when a full equivalent of Na+ is present. As Na+ is added to a solution of Compound 16, the only change observed in the cyclic voltammogram is a slight displacment of the redox couple to more positive potential accompanied by a slight increase in irreversibility. This behavior is almost exactly paralleled by 4-nitrotoluene (Compound 27), a compound which is a model for the sidearm, but not for the entire lariat ether structure.

Thus, compounds having all three features, i.e., macroring, sidearm and electron-deficient aromatic, but in which the geometrical disposition of the components precludes interaction between the ring-bound metal ion and a sidearm donor group, are excluded from the invention. This is shown above in the direct comparion of Compounds 1 to 4 and Compounds 13 to 16 in which novel Structures 1 and 13 are operable as switching devices in the instant invention but Compounds 4 and 16, although cation binders, are not switching devices. Thus, all the compounds claimed herein have utility as cation binders although not all are switching devices.

The increase in stability constant when Compound 13 is in the radical anion form compared to the neutral form is approximately 25,000. This enormous increase in cation binding strength exceeds that observed for the C-pivot systems in which the analogous increase was substantial, but only 750-fold. This superior binding strength is anticipated for N-pivot systems since they are inherently more flexible than the corresponding C-pivot molecules. More important, however, is that not only can these compounds be used as effective switches, they also exhibit binding constants which have magnitudes substantially higher than for common crown ethers.

Structures of the compounds synthesized in the examples herein are found in TABLE 3.

TABLE 1

Electrochemical Data for Na+-Effect on Nitroaromatics

| Compound | Couple[a] | Na+/L ratio[b] | $E_p^{red}(v)$ | $E_p^{ox}(v)$ | $E^{ol}(v)$[c] |
|---|---|---|---|---|---|
| 1 | A | 0 | −1.36 | −1.21 | −1.28 |
|  | A | ½ | −1.38 | −1.18 | −1.28 |
|  | A | 1 | — | — | — |
|  | B | 0 | — | — | — |
|  | B | ½ | −1.17 | −1.04 | −1.11 |
|  | B | 1 | −1.22 | −1.00 | −1.11 |
| 24 | C | 0 | −1.36 | −1.22 | −1.29 |
|  | C | ½ | −1.37 | −1.21 | −1.29 |
|  | C | 1 | −1.37 | −1.21 | −1.29 |
|  | D | 0 | — | — | — |
|  | D | ½ | −1.20 | −0.87 | — |
|  | D | 1 | −1.20 | −0.78 | — |
| 4 | — | 0 | −1.28 | −1.15 | −1.22 |
|  | — | ½ | −1.28 | −0.99 | — |
| 25 | — | 0 | −1.29 | −1.17 | −1.23 |
|  | — | ½ | −1.33 | −1.17 | −1.25 |

[a] See Figure
[b] L = Nitroaromatic (ligand)
[c] Diffusion coefficients for reduced and oxidized forms were assumed to be equal.

TABLE 2

Effect of Na+ on Nitroaromatic Electrochemistry

| Compound Number | Couple Code* | Na+/L (Eq.) | Ep(c) Volts | Ep(a) Volts | E° Volts |
|---|---|---|---|---|---|
| 13 | A | 0 | −1.28 | −1.05 | −1.16 |
|  | A | 0.25 | −1.28 | −1.04 | −1.16 |
|  | A | 0.33 | −1.29 | −1.04 | −1.17 |
|  | A | 0.50 | −1.26 | −1.05 | −1.16 |
|  | A | 1.00 | — | — | — |
|  | B | 0 | — | — | — |
|  | B | 0.25 | −0.97 | −0.82 | −0.90 |
|  | B | 0.33 | −0.98 | −0.82 | −0.90 |
|  | B | 0.50 | −0.98 | −0.82 | −0.90 |
|  | B | 1.00 | −1.00 | −0.80 | −0.90 |
| 26 | C | 0 | −1.29 | −1.05 | −1.17 |
|  | C | 0.50 | −1.30 | −1.05 | −1.18 |
|  | C | 1.00 | −1.29 | −1.05 | −1.17 |
| 16 | — | 0 | −1.18 | −0.97 | −1.08 |
|  | — | 0.50 | −1.17 | −0.95 | — |
|  | — | 1.0 | −1.15 | −0.92 | — |
| 27 | — | 0 | −1.24 | −1.00 | −1.12 |
|  | — | 0.50 | −1.25 | −1.01 | — |
|  | — | 1.00 | −1.25 | −1.01 | — |

Abbreviations:
L = ligand; Ep(c) = cathode potential; Ep(a) = anode potential; Eq. = equivalents.
*Refers to FIG. 3

TABLE 3

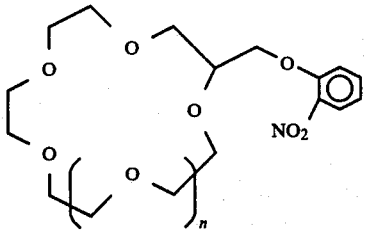

| Structure | Compound number | Ring size |
|---|---|---|
|  | 1, n = 1 | 15 |
|  | 2, n = 2 | 18 |
|  | 3, n = 3 | 21 |

TABLE 3-continued

| Structure | Compound number | Ring size |
|---|---|---|
| (15-/18-/21-crown with CH₂-O-C₆H₄-NO₂ sidearm) | 4, n = 1<br>5, n = 2<br>6, n = 3 | 15<br>18<br>21 |
| (crown with CH₂-O-C₆H₃(NO₂)₂ sidearm) | 7, n = 1<br>8, n = 2<br>9, n = 3 | 15<br>18<br>21 |
| (crown with CH₂-O-C₆H₄-NO₂ sidearm, meta) | 10, n = 1<br>11, n = 2<br>12, n = 3 | 15<br>18<br>21 |
| (aza-crown with N-CH₂-C₆H₄-NO₂ sidearm) | 13, n = 1<br>14, n = 2<br>15, n = 3 | 15<br>18<br>21 |
| (aza-crown with N-CH₂-C₆H₄-NO₂ sidearm, para) | 16, n = 1<br>17, n = 2<br>18, n = 3 | 15<br>18<br>21 |
| (crown with CH₂-O-C₆H₄-CN sidearm) | 19, n = 1<br>20, n = 2<br>21, n = 3 | 15<br>18<br>21 |
| (diaza-crown with two N-CH₂-C₆H₄-NO₂ sidearms) | 22, n = 1<br>23, n = 2 | 15<br>18 |
| 2-nitroanisole | 24 | — |
| 4-nitroanisole | 25 | — |
| 2-nitrotoluene | 26 | — |
| 4-nitrotoluene | 27 | — |

We claim:

1. The electrochemical process of forming a radical anion of a heteromacrocyclic ring compound composed of a substituted heteromacrocyclic ring containing 12–36 contiguous atoms selected from the group C, N, O or S, said N, O or S being separated by at least two carbon atoms, one or more of said ring C or N atoms having attached thereto a substituted or unsubstituted sidearm consisting of C, N, O of S, said sidearm having attached thereto at the other terminus thereof a substituted carbocyclic aromatic or substituted or unsubstituted heteroaromatic residue containing at least one uncharged Lewis basic donor group, the reduction potential of said residue being less than 2.0 V vs. SCE, said sidearm being of sufficient length and flexibility, such that the donor group on or part of the residue will position itself over the macroring cavity to interact with any ring bound cation which is present, which comprises electron transfer thereto.

* * * * *